(12) United States Patent
Matsuura

(10) Patent No.: US 7,753,895 B2
(45) Date of Patent: Jul. 13, 2010

(54) SPERM COLLECTING APPARATUS

(75) Inventor: Tsutomu Matsuura, Tokyo (JP)

(73) Assignee: TENGA Co., Ltd., Tokyo (JP)

( * ) Notice: Subject to any disclaimer, the term of this patent is extended or adjusted under 35 U.S.C. 154(b) by 150 days.

(21) Appl. No.: 11/890,441

(22) Filed: Aug. 6, 2007

(65) Prior Publication Data

US 2008/0065033 A1    Mar. 13, 2008

(51) Int. Cl.
*A61F 5/44* (2006.01)
(52) U.S. Cl. .................. 604/349; 604/317; 604/346; 604/347; 604/353; 128/842; 128/843; 128/844
(58) Field of Classification Search ................ 604/317, 604/346, 347, 349, 353; 128/842–844
See application file for complete search history.

(56) References Cited

U.S. PATENT DOCUMENTS

| 5,437,652 A | * | 8/1995 | Anatolievich | ............ 604/349 |
| 5,782,818 A | * | 7/1998 | Shubin | ................ 604/349 |
| 5,807,360 A | | 9/1998 | Shubin | |
| 5,885,233 A | * | 3/1999 | Adachi | ................ 601/138 |
| 6,113,532 A | * | 9/2000 | Yap | .................... 600/38 |
| 6,149,580 A | | 11/2000 | Dabney | |

FOREIGN PATENT DOCUMENTS

| JP | 07-080017 A | 3/1995 |
| JP | 3016874 U | 8/1995 |
| JP | 3076183 U | 12/2000 |
| JP | 3076627 U | 1/2001 |

* cited by examiner

*Primary Examiner*—Tatyana Zalukaeva
*Assistant Examiner*—Ilya Y Treyger
(74) *Attorney, Agent, or Firm*—Masuvalley & Partners

(57) ABSTRACT

A sperm collecting apparatus is provided and includes a container having a non-cylindrical container main unit whose one end face in a longitudinal direction is open and a cap that is attachable the container main unit. A core member made from a gel-like material, which is located in the container main unit and has an insertion room extending to an inner portion of the core member from an insertion port at one end face in the core member. A sponge layer which is interposed between the core member and an inner wall of the container main unit, the container main unit is a non-cylindrical member whose intermediate portion in a longitudinal direction thereof has an outer diameter smaller than those in both end portions.

23 Claims, 17 Drawing Sheets

A-A

A-A

A-A

SPERM COLLECTING APPARATUS

TECHNICAL FIELD

The present invention relates to a sperm collecting apparatus, and in particular relates to an improvement of conventionally-used sperm collecting apparatuses based on social demands, such as medical researches, demands for medical treatment, prevention of sex-related crimes, antiprostitution activities, and prevention of spreading of venereal diseases, and the like.

BACKGROUND OF THE INVENTION

Various sperm collecting apparatuses for collecting men's sperm have been proposed for necessities of medical research or treatment. For example, a sperm collecting apparatus is used for medical needs such as examination of sexual function of a husband from the sperm collected for examination of the cause of a marital infertility, or treatment of sexual dysfunction, and reservation and storage of the sperm for artificial insemination. Simple sperm collecting apparatuses that can be conventionally available at a low price and that do not cause sanitary or health problems due to the disposability thereof have been known, and they can satisfy various social needs, such as prevention of sex-related crimes, antiprostitution activities, and a decrease of the number of infected persons by venereal diseases, and by satisfying individual sexual desire.

For example, Japanese Utility Model Registration No. 3076627 has proposed a sperm collecting apparatus where an interior member made from a gel-like synthetic resin (styrene block copolymer (styrene thermoplastic elastomer)) having a deep recessed space inside is provided in a cylindrical container main unit, a plurality of small projections projecting to the recessed space and fold-shaped portions are provided inside the interior member, and an exterior member made from urethane resin is provided so as to cover the circumference of the interior member.

In the sperm collecting apparatus, one end of the cylindrical container main unit whose upper and lower faces are flat is opened, an assembly obtained by assembling the exterior member to the interior member so as to cover the circumference thereof is inserted into the container from the opening, an insertion port of the interior member positioned on the side of the opening of the container is closed by a disk-like sponge lid, and the opening of the container is then sealed by a cap. A cross-shaped cut is preliminarily formed at a central portion of the sponge lid so that a penis can be inserted into the interior member via the sponge lid by causing the cut to communicate with the insertion port of the interior member.

The above conventional container main unit is configured as a cylindrical member using a plastic material with desired hardness and thickness so as to have a diameter (about 5 to 6.5 cm) equal over its entire length. Therefore, pressure applied to a penis inside the insertion member from an inner wall of the container main unit via the exterior member becomes approximately even during an operation for penis rubbing, which results in a tendency of simplification of stimulations to the penis. When an elderly person, a disabled person or the like who does not wish for strong stimulations as compared with a healthy young male who uses such a sperm collecting apparatus, there is often a case that pain increases due to excessively strong stimulations, and a sperm collection purpose cannot be achieved. That is, it is difficult to adjust stimulations according to individual reaction or liking. On the contrary, there is a limitation for a user who does not respond to an ordinary stimulation obtains stronger stimulations corresponding to his liking in view of the structure of the container.

Particularly, since an outer shape of the container main unit is formed in a cylinder having a diameter equal over its entire length, it is not easy to compress the container main unit in an inner diametrical direction thereof to elastically deform the same with a grasping power of a person, so that it has been difficult to adjust pressure applied to his penis by pressure-deforming the container main unit with his grasping power when he holds the container main unit with his hand to insert his penis into the container main unit (in the recessed space in the interior member) and conducts a collecting action while rubbing against his penis.

Since the recessed space in the interior member is sealed except for the insertion port, when a user inserts his penis into the recessed space from the insertion port, a space is formed between the interior member inner wall and his penis, the degree of tight contact between the both tends to lower. Particularly, since air tends to be easily accumulated between the most sensitive penis distal end and a depth portion of the recessed space, a problem occurs that accumulated air cannot be discharged even if any strong rubbing action is repeated and sufficient stimulations required for ejaculation cannot be obtained. Even if degassing is tried with strong grasp of the container main unit, since a distance between the inner wall of the container main unit having an equal diameter over its entire length (namely, a cylindrical shape) and the interior member inside the container main unit is about 2 cm, application of sufficient and appropriate pressure cannot be conducted and it is impossible to conduct degassing without imparting pain to a penis.

Since the container has a cylindrical shape with a diameter equal over its entire length, the exterior member covering the circumference of the interior member has a cylindrical shape similar to the container, and the inner wall of the exterior member has a straight shape that does not include any undulation, so that a force for retaining and shape-holding the interior member disposed inside the exterior member cannot be developed sufficiently, deformation of the interior member inside the exterior member becomes free beyond necessity, and buckling or deformation of the interior member tends to occur, so that normal use becomes difficult when the buckling occurs.

Since an elastomer that configures the interior member is expensive, it is effective for total cost reduction to thin the thickness of the interior member to reduce material cost, but when the thickness of the interior member is thinned, the interior member tends to buckle at a time of insertion or a rubbing operation of a penis, which can result in an unusable state.

A proper amount of lubricating liquid (lotion) is also charged in the recessed space for improving a lubricating property between the inner wall of the recessed space of the interior member made from the elastomer and a penis, but when the collecting apparatus is placed upright such that the cap side of the cylindrical container main unit faces downwardly during transportation, storage and display of the collecting apparatus, the insertion port side of the interior member always faces downwardly so that much lubricating liquid passes through the cut of the sponge lid to accumulate on the opening side of the container main unit, or inside the cap. In this state, when the cap is detached, lubricating liquid spills out from the opening of the container to the outside to drop on an outer face of the container or adhere on a hand or cloths of a user, thereby causing discomfort or causing a state that an amount of lubricating liquid in the recessed space of the interior member becomes insufficient during actual use.

In order to deal with such a drawback, it is necessary to store or display a collecting apparatus having a configuration in a state that a container thereof is disposed upright such that a bottom portion thereof opposed to an opening portion of a container main unit faces downwardly, but when the container is placed upright such that the opening portion faces upwardly, lubricating liquid accumulates in only inner bottom portion (depth portion) of the recessed space of the interior member, so that lubricating liquid at an inlet (insertion port) of the recessed space and the inner wall is put in dried state, which can obstruct penis insertion, can cause buckling or deformation of the interior member due to an excessive increase of frictional resistance between a penis and the inner wall of the recessed space, or can cause injury of the penis.

Conventionally, since a peripheral edge of the opening portion of the container main unit repeatedly abuts on a proximal portion of user's penis or skin around his penis during use, there can be a drawback that such portions are injured or discomfort is given to the user.

The container main unit of the sperm collecting apparatus described in Japanese Utility Model Registration No. 3076627 is a cylinder formed using a plastic material having approximately uniform entire thickness, hardness, and elasticity, a diameter (about 5 to 6.5 cm) thereof is equal over an entire length thereof, and it has difficulty in elastic deformation due to its relatively high hardness. Accordingly, pressure applied to a penis inside the insertion member from an inner wall of the container main unit via the exterior member becomes approximately even during an operation for penis rubbing, which results in a tendency of simplification of stimulations to the penis. When an elderly person, a disabled person or the like who does not wish for strong stimulations as compared with a healthy young male who uses such a collecting apparatus, there is often a case that pain increases due to excessively strong stimulations and a sperm collection purpose cannot be achieved. That is, it is difficult to adjust stimulations according to individual reaction or liking. On the contrary, in view of the structure of the container, there is a limitation for a user who does not respond to an ordinary stimulation to obtain strong stimulations corresponding to his liking.

Particularly, since an outer shape of the container main unit is formed in a cylinder having a diameter equal over its entire length and it is difficult to deform the container main unit partially, it is not easy for the user to swing a portion of the container main unit in a direction other than a longitudinal direction of the container main unit except for a reciprocating operation in the longitudinal direction performed while holding the container main unit, and when the user holds the container main unit to insert his penis into the container main unit (in the recessed space in the interior member) and performs a collecting operation for sperm while rubbing on his penis, it is difficult for him to adjust pressure or stimulations applied to his penis, particularly, to the glans of his penis, by swinging a portion of the container main unit.

Regarding the problems except for the above-described ones, the problems described in a first conventional example apply to a second conventional example as they are. That is, the problem of difficulty of degassing due to the fact that the recessed space in the interior member is a sealed space, the problem that a force for retaining and shape-maintaining the interior member disposed in the exterior member is not developed sufficiently and deformation of the interior member in the exterior member becomes excessively free so that the interior member is buckled, the problem of buckling due to the fact that the interior member is formed thinly, the problem of lotion leakage, the problem that the insertion port or the inner wall are dried when the container main unit is kept such that the opening portion faces upwardly, and the problem of feeling of discomfort during use also apply to the second conventional example.

In the sperm collecting apparatus disclosed in Japanese Utility Model Registration No. 3076627, since the interior member only has the single insertion port and a recessed space communicating therewith, the apparatus has to be of a disposable type for hygienic reasons, which is not economical for users.

Regarding the problems except for the above-described ones, the problems described in the first and second conventional examples apply to a third example as they are. That is, the problem of difficulty of degassing due to the fact that the recessed space in the interior member is a sealed space, the problem that a force for retaining and shape-maintaining the interior member disposed in the exterior member is not developed sufficiently and deformation of the interior member in the exterior member becomes excessively free so that the interior member is buckled, the problem of buckling due to the fact that the interior member is formed thinly, the problem of lotion leakage, and the problem of feeling of discomfort during use also apply to the third conventional example.

SUMMARY OF THE INVENTION

One object of a first invention corresponding to the first conventional example is to eliminate the drawback that, when the container is a cylindrical member having a diameter approximately equal over its entire length, pressure applied to a penis in a core member (the interior member) made from a gel-like resin material becomes even over the entire length of the penis during an operation for penis rubbing so that stimulations to the penis are simplified to achieve the sperm collection purpose by applying optimal and necessary and sufficient stimulations suitable for him, even when not only a healthy young male but also an elderly person, a disabled person or the like who is susceptible to stimulations as compared with a healthy young male who uses such a sperm collecting apparatus. A user who requires stimulations stronger than ones required for an ordinary user can also achieve this purpose sufficiently.

Particularly, another object is to adjust pressure applied to a penis in the container main unit by providing undulation to an outer shape or a diameter size of the container main unit in advance to provide a portion of the container main unit easily deformed according to external pressure and by elastically deforming the container main unit according to a grasping power of a user, thereby fluctuating stimulations to the penis.

Furthermore, another object is to conduct degassing without delay at a time of insertion and rubbing of a penis in order to eliminate the drawback that due to that air is accumulated between a distal end of the penis and the inner depth portion of the core member when the penis is forcibly inserted into the core member made from gel-like resin in the container, rubbing between the distal end of the penis and the inner wall of the core member becomes insufficient in a rubbing operation performed thereafter so that stimulations required for erection and ejaculation cannot be obtained.

Further, another object is to eliminate the drawback that, since the container is formed in a cylindrical shape having a diameter equal over its entire length, the interior member disposed inside an inner portion of the exterior member is easily buckled and deformed at a time of insertion and rubbing of a penis so that normal use of the container becomes difficult when buckling is caused.

Further, another object is to provide a sperm collecting apparatus which can prevent lubricating liquid (lotion) charged in the core member from leaking from the insertion port of the core member at an opening time of a cap even if the sperm collecting apparatus unused is placed upright with the opening side of the container facing downwardly such that the lubricating liquid accumulates in the inlet side of the core member while the sperm collecting apparatus unused is being stored or displayed.

Further, another object is to eliminate the drawback that due to repetitive abutting of a peripheral edge of the opening portion of the container main unit on a proximal portion of user's penis or skin around his penis during use of the container main unit, a body portion of the user on which the peripheral edge abuts is injured or the user feels discomfort about the use.

A second invention corresponding to the second conventional example is to eliminate the drawback that, when the container is a cylindrical member having an approximately equal diameter and an approximately even hardness (even elasticity) over its entire length, pressure applied to a penis in a core member (the interior member) made from a gel-like resin material becomes uniform over the entire length of the penis during an operation for penis rubbing so that stimulations to the penis are simplified to achieve a sperm collection purpose by applying optimal and necessary and sufficient stimulations suitable for him, even when not only a healthy young male but also an elderly person, a disabled person or the like who is susceptible to stimulations as compared with a healthy young male who uses such a sperm collecting apparatus. A user who requires stimulations, pressure, and deformation stronger than those required for an ordinary user can also achieve this purpose sufficiently.

Particularly, another object is to adjust pressure applied to a penis in the container main unit by providing undulation to an outer shape or diametrical size of the container main unit in advance to provide a portion easily deformed in a direction except for a longitudinal direction at at least one portion of the container main unit according to external pressure and by elastically deforming the container main unit according to a grasping force of a user, thereby changing stimulations to the penis.

Further, another object is to conduct degassing without delay at a time of insertion and rubbing of a penis in order to eliminate the drawback that due to that the air is accumulated between a distal end of the penis and the inner depth portion of the core member when the penis is forcibly inserted into the core member made from a gel-like resin in the container, rubbing between the distal end of the penis and the inner wall of the core member becomes insufficient in a rubbing operation performed thereafter so that stimulations required for erection and ejaculation cannot be obtained.

Further, another object is to solve the problem that, since the container is formed in a cylindrical shape having a diameter equal over its entire length, the interior member disposed inside an inner portion of the exterior member is easily buckled and deformed at a time of insertion and rubbing of a penis so that normal use of the container becomes difficult when buckling is caused.

Further, another object is to provide a sperm collecting apparatus which can prevent lubricating liquid (lotion) charged in the core member from leaking from the insertion port of the core member at an opening time of a cap even if the sperm collecting apparatus unused is disposed upright with the opening side of the container facing downwardly such that the lubricating liquid accumulates in the inlet side of the core member when an unused collecting apparatus is being stored or displayed.

Further, another object is to eliminate the drawback that due to repetitive abutting of a peripheral edge of the opening portion of the container main unit on a proximal portion of a user's penis or skin around his penis during use of the container main unit, a body portion of the user on which the peripheral edge of the opening portion abuts is injured or the user feels discomfort about the use.

An object of a third invention corresponding to the third conventional example is to double the number of uses to improve economic efficiency and to achieve cost reduction by providing two insertion ports in a core member accommodated in one container and an insertion room communicating with the respective insertion ports.

Further, another object is to conduct degassing without delay at a time of insertion and rubbing of a penis in order to eliminate the drawback that due to that the air is accumulated between a distal end of a penis and the inner depth portion of the core member when the penis is forcibly inserted into the core member made from a gel-like resin in the container, rubbing between the distal end of the penis and the inner wall of the core member becomes insufficient in a rubbing operation performed thereafter so that stimulations required for erection and ejaculation cannot be obtained.

Further, another object is to eliminate the drawback that since the container is formed in a cylindrical shape having a diameter equal over its entire length, the interior member disposed inside an inner portion of the exterior member is easily buckled and deformed at a time of insertion and rubbing of a penis so that normal use of the container becomes difficult when buckling is caused.

Further, another object is to provide a sperm collecting apparatus which can prevent lubricating liquid (lotion) charged in the core member from leaking from the insertion port of the core member at an opening time of a cap even if the sperm collecting apparatus unused is placed upright with the opening side of the container facing downwardly such that the lubricating liquid accumulates in the inlet side of the core member while the collecting apparatus unused is being stored or displayed.

Further, another object is to eliminate the drawback that due to repetitive abutting of a peripheral edge of an opening portion of the container main unit on a proximal portion of a user's penis or skin around his penis during use of the container main unit, a body portion of the user on which the peripheral edge of the opening portion abuts is injured or the user feels discomfort about the use.

A sperm collecting rate can be improved according to diversification of variations of stimulations. A user can select an insertion recess to be used according to his liking.

In order to achieve the object of a first invention, the invention is a sperm collecting apparatus including: a container having a non-cylindrical container main unit whose one end face in a longitudinal direction is opened and a cap that is attached to and detached from an opening portion of the container main unit to open and close the opening portion; a core member made from a gel-like resin, which is accommodated in the container main unit and has an insertion room extending to an inner portion of the core member from an insertion port at one end face in a longitudinal direction in the core member; and a sponge layer which is interposed between the core member and an inner wall of the container main unit, characterized in that the container main unit is a non-cylindrical member whose intermediate portion in a longitudinal direction thereof has an outer diameter smaller than those in both end portions thereof in the longitudinal direction, an upper face of the cap is a flat face suitable for stationary placement, and an end portion of the container main unit opposed to the opening portion is formed in an arc face (a spherical face) which is not suitable for stationary placement.

The invention is characterized in that an inner diameter of the insertion room of the core member corresponding to the small diameter portion provided on the intermediate portion of the container main unit is smaller than an inner diameter of another portion of the insertion room.

The invention is also characterized in that an outer diameter of an end portion of the non-cylindrical container main unit at a depth side is smaller than that of an end portion thereof at the opening portion side.

Another embodiment of the invention is a sperm collecting apparatus including: a container having a non-cylindrical container main unit whose one end face in a longitudinal direction is opened and a cap that is attached to and detached from an opening portion of the container main unit to open and close the opening portion; a core member made from gel-like resin, which is accommodated in the container main unit and has an insertion room extending to an inner portion of the core member from an insertion port at one end face in a longitudinal direction in the core member; and a sponge layer which is interposed between the core member and an inner wall of the container main unit, characterized in that an outer shape of the non-cylindrical container is formed such that an end face of the non-cylindrical container at the opening portion side is a circular flat face, a side face width is gradually decreased toward an intermediate portion in a longitudinal direction thereof to be flattened, and a side face width of the depth end portion is made minimal.

This embodiment is characterized in that the core member includes a projecting rib projecting on an outer peripheral face thereof, and the sponge layer includes a holding portion which holds the rib to prevent buckling of the core member.

The invention is also characterized in that a lid plate that tightly contacts with the core member to close the insertion port is disposed at the insertion port of the core member.

The invention is also characterized in that a sponge lid having a cut is interposed between an end face of the core member at the insertion port side and the cap, and a portion of the sponge lid is protruded beyond an end edge of the opening portion of the container main unit to the outside.

The invention is also characterized in that a cut line for degassing serving as a check valve is formed at a proper portion in a distal end portion of the core member.

The invention is also characterized in that a bottom portion sponge layer different from the sponge layer is interposed between an inner bottom face of the container main unit and a distal end face of the core member.

The invention is also characterized by further including an inner cap having a projecting portion which is fitted in the insertion port of the core member from the outside to close the insertion port and a supporting face which supports the projecting portion and contacts with one end face of the core member in the longitudinal direction.

The invention is also characterized in that a room for accumulating lotion for insertion is formed between the supporting face of the inner cap and one end face of the core member in the longitudinal direction.

The invention is also characterized in that a flange portion is formed at one end face of the core member in the longitudinal direction, an outer peripheral edge of the flange portion bulges beyond the opening portion of the container main unit in an outer diametrical direction, and the outer peripheral edge of the flange portion is kept in an outwardly folded state such that the outer peripheral edge of the flange portion covers an end edge of the opening portion of the container main unit.

In order to achieve the object of a second invention, the invention is a sperm collecting apparatus including: a container having a cylindrical container main unit whose one end face in a longitudinal direction is opened and a cap that is attached to and detached from an opening portion of the container main unit to open and close the opening portion; and a core member made from a gel-like resin, which is accommodated in the container and has an insertion room extending to an inner portion of the core member from an insertion port at one end face in a longitudinal direction in the core member, characterized in that the container main unit includes at least one easily deformable portion more deformable than another portion at a proper portion in an intermediate portion in the longitudinal direction.

The invention is a sperm collecting apparatus including: a container having a cylindrical container main unit whose one end in a longitudinal direction is opened and a cap that is attached to and detached from an opening portion of the container main unit to open and close the opening portion; a core member made from a gel-like resin, which is accommodated in the container main unit and has an insertion room extending to an inner portion of the core member from an insertion port at one end face in a longitudinal direction in the core member; and a sponge layer which is interposed between the core member and an inner wall of the container main unit, characterized in that the container main unit includes an easily deformable portion more deformable than another portion at a proper portion in an intermediate portion in the longitudinal direction.

The invention is characterized in that an upper face of the cap is a flat face suitable for stationary placement and an end portion of the container main unit opposed to the opening portion is formed in an arc face which is not suitable for stationary placement.

The invention is also characterized in that the easily deformable portion swingably supports one end side of the container in a longitudinal direction thereof to the other end side thereof.

The invention is also characterized in that the easily deformable portion supports one end side of the container in a longitudinal direction thereof such that the one end side is capable of expanding and contracting in the longitudinal direction to the other end side thereof.

The invention is also characterized in that the easily deformable portion is formed of either one of an accordion-shaped portion, a thin portion, a soft material portion, a mesh portion, and a corrugated portion.

The invention is also characterized in that the core member includes a projecting rib projecting on an outer peripheral face thereof, and the sponge layer includes a holding portion which holds the rib to prevent buckling of the core member.

The invention is also characterized in that a lid plate that tightly contacts with the core member to close the insertion port is disposed at the insertion port of the core member.

The invention is also characterized in that a sponge lid having a cut is interposed between an end face of the core member at the insertion port side and the cap, and a portion of the sponge lid is protruded beyond an opening portion end edge of the container main unit to the outside.

The invention is also characterized in that a cut line for degassing serving as a check valve is formed at a proper portion at a distal end portion of the core member.

The invention is also characterized in that a sponge lid is interposed between an end face of the core member at the insertion port side and the cap, a through-hole is formed at a central portion of the sponge lid and a fitting member that closes the through-hole is fitted into the through-hole, so that the fitting member can be caused to fall off from the through-hole by a pressing force applied from the opening portion side of the container main unit to be moved from the insertion port of the core member into the insertion room.

The invention is also characterized in that an upper face of the cap is a flat face suitable for stationary placement and an end portion of the container main unit opposed to the opening portion is formed in an arc face (a spherical face) which is not suitable for stationary placement.

The invention is also characterized in that a bottom portion sponge layer different from the sponge layer is interposed between an inner bottom face of the container main unit and a distal end face of the core member.

The invention is also characterized by further including an inner cap having a projecting portion which is fitted in the insertion port of the core member from the outside to close the insertion port and a supporting face which supports the projecting portion and contacts with one end face of the core member in the longitudinal direction.

The invention is also characterized in that a flange portion is formed at one end face of the core member in the longitudinal direction, an outer peripheral edge of the flange portion bulges beyond the opening portion of the container main unit in an outer diametrical direction, and the outer peripheral edge of the flange portion is kept in an outwardly-folded state such that the outer peripheral edge of the flange portion covers an end edge of the opening portion of the container main unit.

In order to achieve the object of a third invention, the invention is a sperm collecting apparatus characterized by including: a container including a non-cylindrical container main unit whose both end faces in a longitudinal direction are opened and two caps that are attached to and detached from respective opening portions of the container main unit to open and close the opening portions; a core member made from a gel-like resin, which is accommodated in the container main unit and has at least two insertion rooms extending to an inner portion of the core member from insertion ports provided in both end faces of the core member in a longitudinal direction in the core member; and a sponge layer which is interposed between the core member and an inner wall of the container main unit.

This embodiment of the invention is characterized in that the non-cylindrical container main unit has a small-diameter portion on a proper outer face at at least one portion.

The invention is also characterized in that inner diameters of the two insertion rooms of the core member are different from each other.

The invention is also characterized in that the sponge lids having a cut are interposed between both end faces of the core member in the longitudinal direction and inner faces of the respective caps.

The invention is also characterized in that the core member includes a projecting rib projecting on an outer peripheral face thereof, and the sponge layer includes a holding portion which holds the rib to prevent buckling of the core member.

The invention is also characterized in that a lid plate that tightly contacts with the core member to close the insertion port is disposed at the insertion port of the core member.

The invention is also characterized in that a portion of the sponge lid is protruded beyond an end edge of the opening portion of the container main unit to the outside.

The invention is also characterized in that a cut line for degassing serving as a check valve is formed on a proper portion at a distal end portion of the core member.

The invention is also characterized by including an inner cap having a projecting portion which is fitted in at least one insertion port of the core member from the outside to close the one insertion port and a supporting face which supports the projecting portion and contacts with one end face of the core member in the longitudinal direction.

The invention is also characterized in that a flange portion is formed on at least one end face of the core member in the longitudinal direction, an outer peripheral edge of the flange portion bulges beyond the opening portion of the container main unit in an outer diametrical direction, and the outer peripheral edge of the flange portion is kept in an outwardly-folded state such that the outer peripheral edge of the flange portion covers an end edge of the opening portion of the container main unit.

The invention is also characterized that a space for accumulating lotion for insertion is formed between the supporting face of the inner cap and one end face of the core member in the longitudinal direction.

According to the first invention, since the container is not a cylindrical member having a diameter approximately equal over its entire length but it is a non-cylindrical member, pressure applied to a penis inside the core member fluctuates during an operation for penis rubbing so that stimulations to the penis are diversified. Therefore, when not only a healthy young male but also an elderly person, a disabled person or the like who is susceptible to stimulations as compared with a healthy young male who uses such a collecting apparatus, a sperm collection purpose can be achieved by applying minimal stimulations suitable for him.

Since a portion easily deformed by external pressure is provided and the easily deformable portion can be elastically deformed by a user's grasping power, pressure applied to his penis inside the core member can be adjusted so that stimulations thereto can be fluctuated. The air that tends to be accumulated in the core member can be removed easily.

By providing a cut line serving as a check valve at a distal end of the core member, the air that tends to be accumulated in the core member can be removed without delay at a time of insertion or rubbing of a penis.

Further, since the intermediate portion of the container is reduced in diameter so that the core member inside the container can be prevented from being moved or deformed, buckling of the core member can be prevented.

Further, since the collecting apparatus unused is placed upright with the opening side of the container facing downwardly such that the lubricating liquid (lotion) accumulates in the inlet side of the core member while the collecting apparatus unused is being stored or displayed, it is made possible to insert his penis smoothly as it is when the cap is opened, and the lubricating liquid is further prevented from leaking from the insertion port of the core member.

Further, a drawback such that due to repetitive abutting of a peripheral edge of an opening portion of the container main unit on a proximal portion of user's penis or skin around his penis during use of the container main unit, a body portion of the user on which the opening portion peripheral edge abuts is injured or the user feels discomfort about the use can be eliminated.

Since the inner cap having a projecting portion which is fitted in the insertion port of the core member from the outside to close the insertion port and a supporting face which supports the projecting portion and contacts with one end face of the core member in the longitudinal direction is provided, leakage of lotion from the insertion port can be prevented.

Since an outer peripheral edge of the flange portion formed on one end face of the core member in the longitudinal direction bulges beyond the opening portion of the container main unit in an outer diametrical direction and the outer peripheral edge of the flange portion is kept in an outwardly-folded state, an end edge of the opening portion of the container main unit is not exposed and it is covered with the soft flange. Accordingly, a state such that a portion of a human body directly rubs on the end edge of the opening portion to cause pain during its use is prevented.

According to the second invention, since the container is not a cylindrical member approximately equal over its entire length (it is a non-cylindrical member) and it has at least one easily deformable portion at a proper point on an intermediate portion thereof, pressure applied to a penis inside the core member and direction thereof can be fluctuated arbitrarily during an operation for penis rubbing so that stimulations to the penis are diversified. Therefore, when not only a healthy young male but also an elderly person, a disabled person or the like who is susceptible to stimulations as compared with a healthy young male who uses such a collecting apparatus, a collection purpose can be achieved by applying minimal stimulations suitable for the user.

Since a portion easily deformed by external pressure or according to an external operation is provided so that it is made possible to swing a portion of the container about the easily deformable portion in front and rear, left and right, and rotating directions except for the longitudinal direction, stimulations can be fluctuated by adjusting pressure applied to a penis inside or changing a portion applied with pressure. The air that tends to be accumulated in the core member can be removed easily.

By providing a cut line serving as a check valve at a distal end of the core member, the air that tends to be accumulated inside the core member can be removed without delay at a time of insertion or rubbing of a penis.

When the easily deformable portion provided at the intermediate portion of the container is formed in an accordion shape, the core member can be applied with pressure in a diametrical direction via an accordion-shaped portion, so that the core member inside is prevented from being moved and deformed, and buckling of the core member can be prevented.

Since the collecting apparatus unused is placed upright with the opening side of the container facing downwardly such that the lubricating liquid (lotion) accumulates in the core member inlet side while the collecting apparatus unused is being stored or displayed, it is made possible to insert his penis smoothly as it is when the cap is opened and the lubricating liquid is prevented from leaking from the insertion port of the core member.

A drawback such that due to repetitive abutting of a peripheral edge of an opening portion of the container main unit on a proximal portion of user's penis or skin around his penis during use of the container main unit, a body portion of the user on which the opening portion peripheral edge abuts is injured or the user feels discomfort about the use can be eliminated.

Since the inner cap having a projecting portion which is fitted in the insertion port of the core member from the outside to close the insertion port and a supporting face which supports the projecting portion and contacts with one end face of the core member in the longitudinal direction is provided, leakage of lotion from the insertion port can be prevented.

Since an outer peripheral edge of the flange portion formed on one end face of the core member in the longitudinal direction bulges beyond the opening portion of the container main unit in an outer diametrical direction and the outer peripheral edge of the flange portion is kept in an outwardly-folded state, an end edge of the opening portion of the container main unit is not exposed and it is covered with the soft flange. Accordingly, a state such that a portion of a human body directly rubs on the end edge of the opening portion to cause pain during use is prevented.

According to the third invention, since use is made possible from the penis insertion ports respectively provided at both end portions of one container in a longitudinal direction thereof, one collecting apparatus can be utilized twice, so that economical efficiency can be improved. Parts having a common specification can be commonly used for the respective opening portion sides, cost reduction can be achieved.

By making the respective insertion recesses different in inner diameter, arrangement of projections or the like, the number of projections, or projection shape, use feeling can be changed. The respective insertion recesses can be used alternatively in one time use, so that variation of stimulations can be expanded by using the two insertion recesses different in stimulations and use feeling in one time use and a sperm collecting efficiency can be improved.

A user can select an insertion recess to be used so as to meet his liking.

By providing a cut line serving as a check valve at a distal end of the core member, the air that tends to be accumulated in the core member can be removed without delay at a time of insertion or rubbing of a penis.

Since the stepped portion or the small diameter portion is provided at one portion of the container, the core member inside can be prevented from being moved or deformed so that buckling of the core member can be prevented.

Since the collecting apparatus unused is placed upright with the opening side of the container facing downwardly such that the lubricating liquid (lotion) accumulates in the core member inlet side while the collecting apparatus unused is being stored or displayed, it is made possible to insert his penis smoothly as it is when the cap is opened and the lubricating liquid is prevented from leaking from the insertion port of the core member.

A drawback such that due to repetitive abutting of an opening portion peripheral edge of the container main unit on a proximal portion of user's penis or skin around his penis during use of the container main unit, a body portion of the user on which the opening portion peripheral edge abuts is injured or the user feels discomfort about the use can be eliminated.

Since the inner cap having a projecting portion which is fitted in either one insertion port of the core member from the outside to close the insertion port and a supporting face which supports the projecting portion and contacts with one end face of the core member in the longitudinal direction is provided, leakage of lotion from the insertion port can be prevented.

Since an outer peripheral edge of the flange portion formed on either one end face of the core member in the longitudinal direction bulges beyond the opening portion of the container main unit in an outer diametrical direction and the outer peripheral edge of the flange portion is kept in an outwardly-folded state, an end edge of the opening portion of the container main unit is not exposed and it is covered with the soft flange. Accordingly, a case such that a portion of a human body directly rubs on the end edge of the opening portion to cause pain during its use can be prevented.

EXPLANATION OF THE CODES

Figure 1:
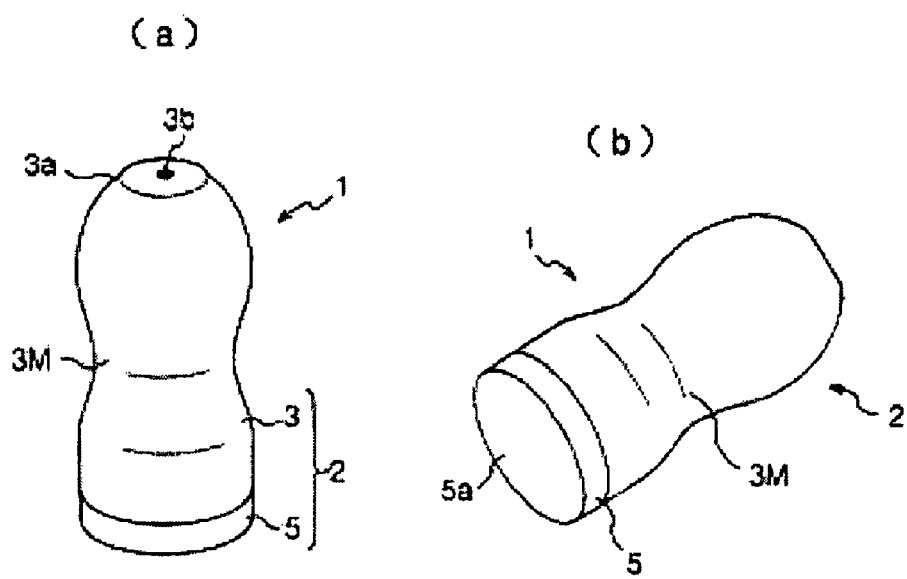
FIGS. 1(a) and 1(b) are appearance perspective views of a sperm collecting apparatus according to a first embodiment of the first invention.

1 Sperm collecting apparatus, 2 Container, 3 Container main unit, 3c Easily deformable portion, 4 Opening portion, 5 Cap, 5a, 5b Cap, 10 Core member, 11 Insertion port, 11a, 11b Insertion port, 12 Insertion room, 12a, 12b Insertion room, 14 Rib, 20 Sponge layer, 30 Sponge member (Bottom sponge layer), 35 Lid plate, 40 Sponge lid, 41 Cut line, 50 Inner cap, 51 Projecting portion, 52 Supporting face (Supporting plate), 60 Flange portion, 60a Outer peripheral edge.

DETAILED DESCRIPTION OF THE PREFERRED EMBODIMENTS

A first invention is explained below in detail by embodiments shown in the drawings.

Figure 2:
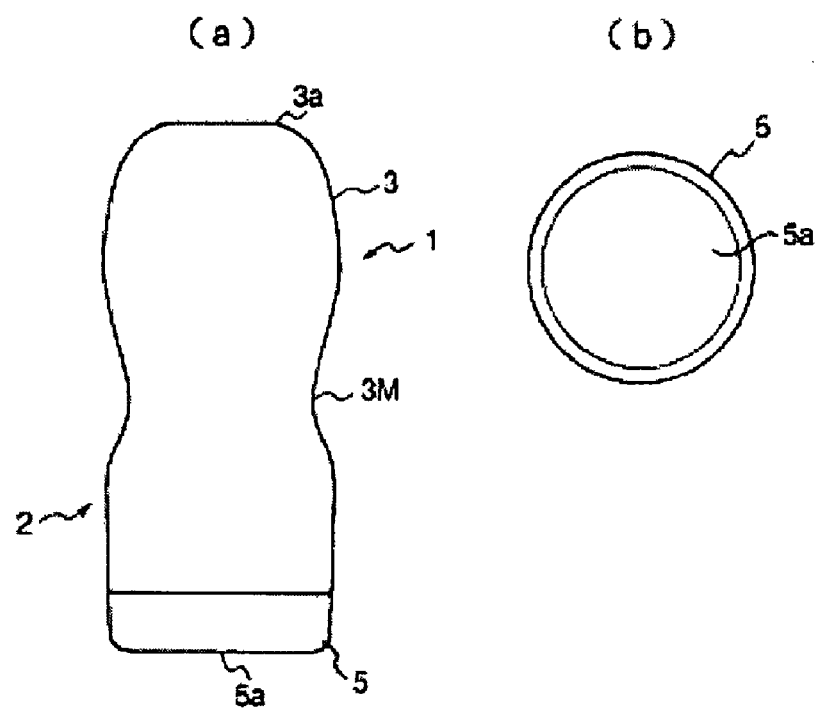
FIGS. 2(a) and 2(b) are a front view and a bottom view of the sperm collecting apparatus
Figure 3:
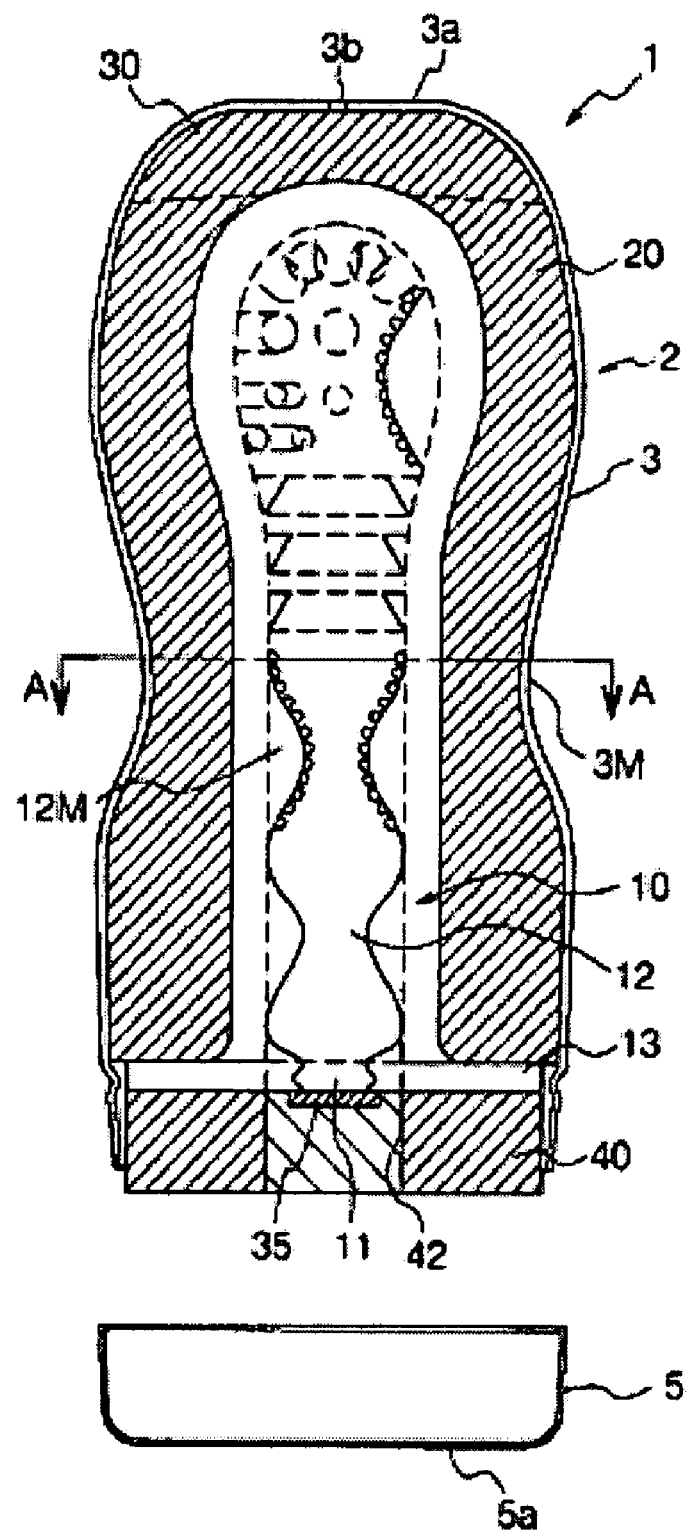
FIG. 3 is a vertical sectional view of the sperm collecting apparatus.
Figure 4:
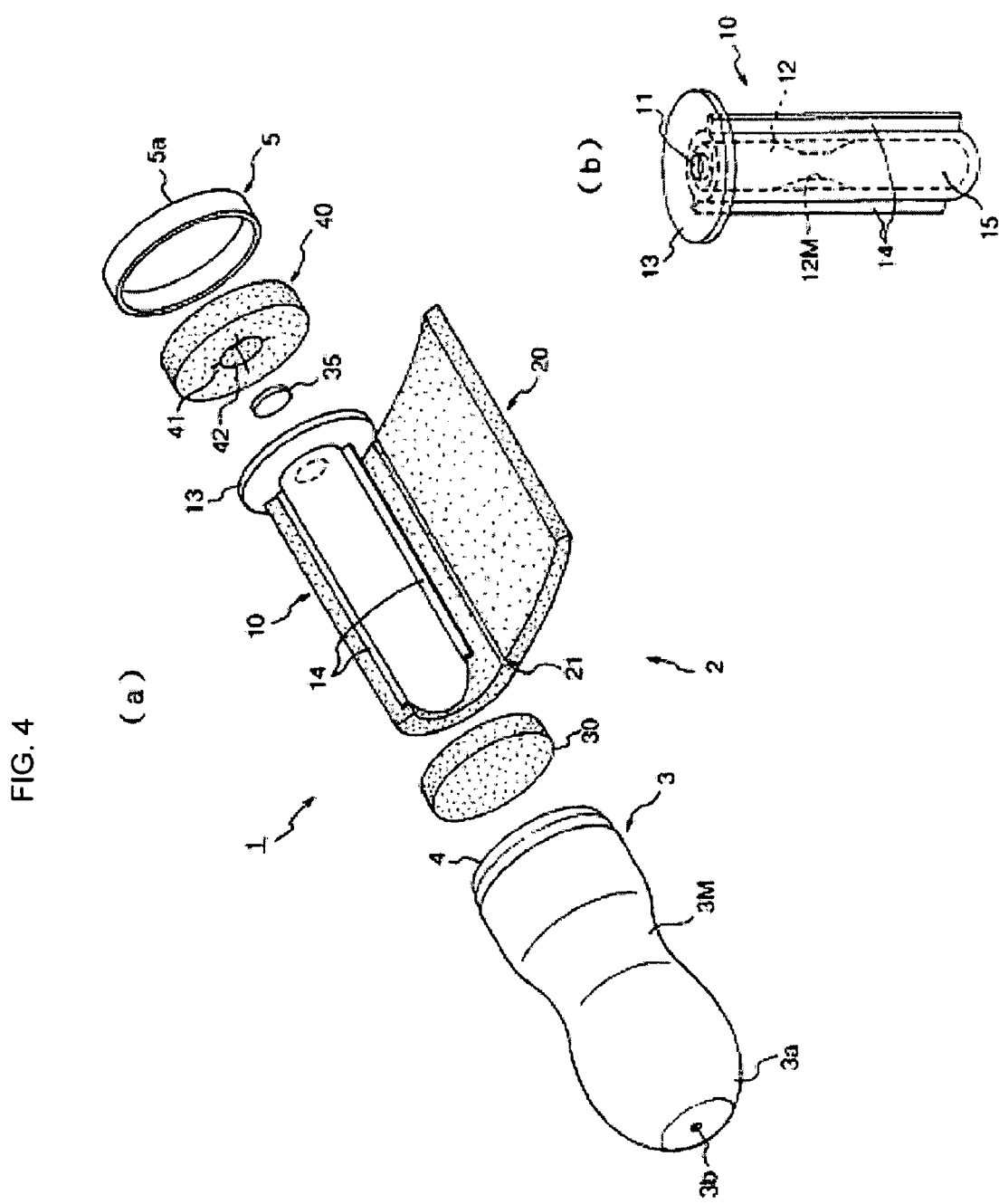
FIGS. 4(a) and 4(b) are an exploded perspective view of respective constituent elements and an appearance perspective view of a core member.
Figure 5:
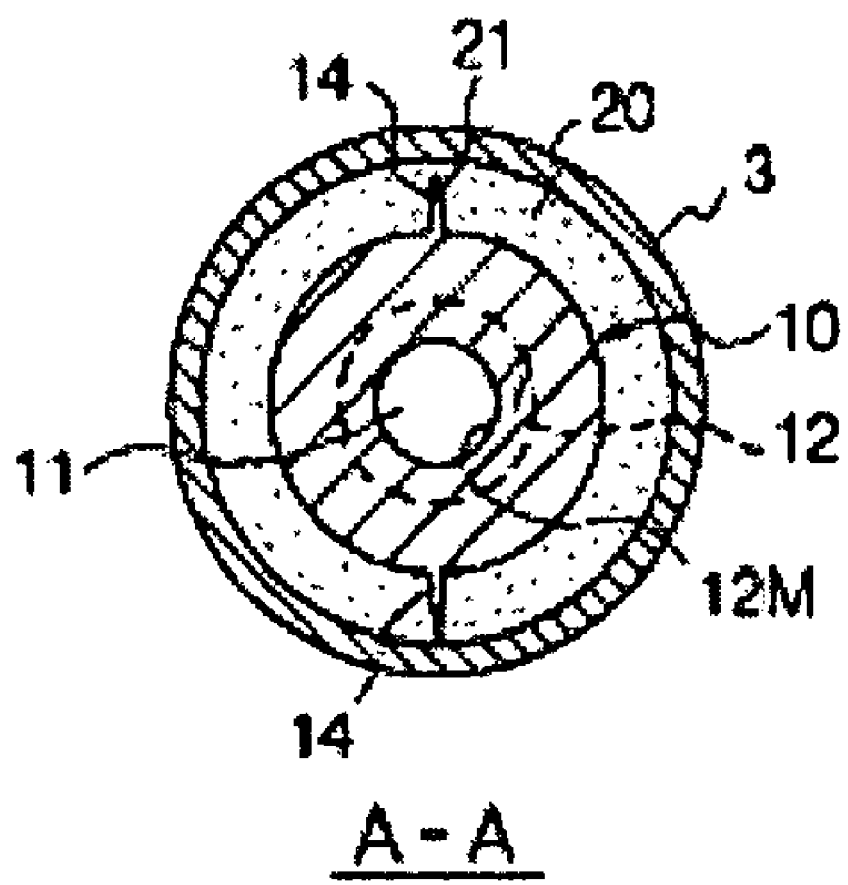
FIG. 5 is a sectional view of line A-A in FIG. 3.

FIGS. 1(a) and 1(b) are appearance perspective views of a sperm collecting apparatus according to a first embodiment of the present invention, FIGS. 2(a) and 2(b) are a front view and a bottom view of the sperm collecting apparatus, FIG. 3 is a vertical sectional view of the sperm collecting apparatus, FIGS. 4(a) and 4(b) are an exploded perspective view of respective constituent elements and an appearance perspective view of a core member, and FIG. 5 is a sectional view of the sperm collecting apparatus taken along line A-A in FIG. 3.

The sperm collecting apparatus 1 includes a container 2 having a non-cylindrical container main unit 3 whose one end face in a longitudinal direction thereof is opened and a cap 5 that is attached to and detached from an opening portion 4 of the container main unit 3 to open and close the opening portion, a core member 10 made from a gel-like resin, that is accommodated in the container main unit 3 and has an insertion room 12 extending from an insertion port 11 at one end face in a longitudinal direction therein, and a sponge layer 20 that is interposed between the core member 10 made from a gel-like resin and an inner wall of the container main unit.

The sperm collecting apparatus 1 includes a sponge member (a bottom sponge layer) 30 disposed on an inner bottom face of the container main unit, a lid plate 35 additionally provided at the insertion port 11 of the core member to close the same, and a sponge lid 40 additionally provided on an end face of the core member 10 at an insertion side and tightly contacts with the inner wall of the container main unit to perform such a function as positioning of the core member 10 or fixing thereof.

The container main unit 3 is made of a resin material with a required thickness, it is a non-cylindrical member where an outer diameter of an intermediate portion 3M is smaller than outer diameters of both end portions in a longitudinal direction, and an upper face 5a of the cap 5 made from a similar resin material is a flat face suitable for stationary placement on a flat place while an end portion 3a of the container main unit 3 positioned to the opening portion 4 has an arc face (a spherical face) that is not suitable for stationary placement. Therefore, the container main unit 3 closed by the cap 5 can be stationarily placed on a flat plane such that the upper face 5a of the cap 5 faces downwardly. On the other hand, since it is difficult to place the other end 3a of the container main unit 3 on a flat plane stably, such a drawback that lubricating liquid accumulates in a depth portion of the insertion room 12 so that lubricating liquid at the inlet side runs dry in an unused state can be eliminated.

A small hole 3b for degassing is preliminarily formed at the other end 3a of the container main unit 3 as necessary and it is preliminarily sealed in the unused state by a seal (not shown). The seal is removed when it is used and the degree of tight contact or feeling of tight contact between the inner wall of the core member and a user's penis can be adjusted by closing and opening the small hole 3b during use with his finger. That is, since the penis tightly contacts with the inner wall of the core member in a closed state of the small hole 3b, a tightening force becomes strong, while the tightening force becomes weak in an opened state of the small hole 3b. It is made possible to fluctuate the tightening force and to fluctuate stimulations according to a simple operation such as only closing and opening the small hole. When the user feels pain in his penis, he can open the small hole.

The core member 10 is a bag-like member made from gel-like resin with viscosity such as elastomer or gel-like rubber, it includes a large-diameter flange 13 at an end face on the insertions side, and the insertion room 12 with a diameter larger than that of the insertion port is formed inside the small-diameter insertion port 11 so as to communicates therewith. A projection(s), a fold(s), or the like is formed in the insertion room 12 with a proper arrangement. A proper amount of lotion or the like serving as lubricating liquid is preliminarily charged in the insertion room 12.

Regarding an inner diameter of the insertion room 12 of the core member, an inner diameter of a portion 12M corresponding to the small-diameter portion 3M provided in the intermediate portion of the container main unit 3 in the longitudinal direction is narrower than inner diameters of the other portions. Therefore, when a penis is forcibly inserted from the insertion port 11 into the insertion room 12, of course, and a distal end of the penis repeatedly passes through the narrowed portion during a rubbing operation, so that pressure to the penis fluctuates, which can result in fluctuation and increase of applied stimulations. Since the intermediate portion of the core member 10 in the longitudinal direction is always pressed by the small-diameter portion 3M of the container main unit, a shape-holding force of the core member is raised, so that buckling of the core member is prevented at a time of insertion and rubbing of a penis.

Ribs 14 extending in an axial direction are integrally formed on an outer peripheral face of the core member 10. The ribs 14 may be ribs extending in a circumferential direction.

A short cut line 15 for degassing serving as a check valve is formed by providing a cut at a proper point on a distal end portion of the core member 10 in advance. Since the cut line 15 is completely closed in a non-insertion state of a penis according to an elastic force of the core member itself, lubricating liquid inside the core member is prevented from leaking and when an internal pressure is increased due to penis insertion, the air that tends to be accumulated between a penis distal end and an inner bottom face of the insertion room 12 can be degassed by opening the cut line 15. After the air is removed, even if an operation for penis rubbing is performed, the cut line 15 continues to close so that lubricating liquid hardly flows to the outside. However, even if a small amount of lubrication liquid leaks from the cut line 15, there will not be such a state that lubricating liquid inside the core member lacks to such an extent that the shortage disturbs use of this apparatus.

By arranging a lid plate 35 that tightly contacts with an end face of the core member around a peripheral edge of the insertion port 11 to openably/closably close the insertion port at the insertion port 11 of the core member 10 to close the insertion port, lubricating liquid charged in the insertion room 12 is prevented from leaking. Accordingly, even when the container 2 is stationarily placed such that the cap 5 side faces downwardly, lubricating liquid does not leak, so that the insertion port side of the insertion room 12 can be maintained in a sufficiently-lubricated state. Reduction of lubricating liquid inside the core member due to drying is prevented owing to presence of the lid plate 35. Drying inside the core member is further prevented by impregnation of lubricating liquid in the sponge lid 40. Since the lid plate 35 is made from a gel-like resin similar to the material for the core member 10, it tightly contacts with the insertion side end face of the core member to tightly close the insertion port 11. On the other hand, when he inserts his penis to the insertion port, the lid plate is pushed into the insertion port by a penis distal end, so that it does not disturb rubbing operations performed thereafter.

A cut line 41 for penis insertion is formed in the sponge lid 40 additionally provided on a face of the flange 13 of the core member in advance, but when the insertion port 11 is closed from the outside using the lid plate 35, a hole 42 fitted with the lid plate 35 can be formed at a central portion of the sponge lid 40 in advance. Thereby, an inside face of the sponge lid 40 can be caused to tightly contact with the face of the flange 13, so that a force for positioning and fixing the core member increases owing to the sponge lid 40. The force for fixing the lid plate 35 increases.

Further, by fitting a fitting member made from sponge (urethane foam) in the hole 42 to close the hole 42 in advance, the fitting member can be pushed into the insertion room at a time of penis insertion. In this case, the fitting member rolls between a penis distal end and the inner wall of the insertion recess so that the penis can be imparted with irregular stimulations.

When the sponge lid 40 having the cut line 41 is interposed between the end face of the core member 10 on the insertion port side and the cap 5, as also shown in FIG. 3, a portion of the sponge lid 40 is protruded beyond the end edge of the opening portion of the container main unit 3 to the outside by a predetermined amount (for example, 3 mm to 5 mm). By adopting this configuration, a drawback such that due to repetitive abutting of an opening portion peripheral edge of the container main unit 3 on a proximal portion of user's penis or skin around his penis during use of the container main unit 3, a body portion of the user on which the opening portion peripheral edge abuts is injured or the user feels discomfort about the use can be eliminated.

Next, the sponge layer 20 is made of a foam resin sheet but is not a simple sheet, and is formed with a holding portion 21 that holds a rib 14 formed on the outer periphery of the core member to prevent buckling of the core member 10. In this embodiment, an example that two plate-like ribs 14 extending in an axial direction are provided is shown, where in order to hold these ribs 14, the core member 10 and the sponge layer 20 are integrated by providing the holding portion 21 formed as a cut line extending in the axial direction in an intermediate portion of the sponge layer 20 in a circumferential direction to hold one rib 14 in the holding portion 21 and holding the other rib 14 between both end faces of the sponge layer 20 in the circumferential direction and the integrated core member 10 and sponge member 20 are inserted into the container main unit 3 from the opening portion 4 side (FIG. 5).

When there are three or more ribs 14, the number of holding portions 21 is increased correspondingly. When a forming direction of the rib 14 is a circumferential direction or another direction, a forming direction of the holding portion is changed similarly.

Based on such contraptions as variation of the thickness of the sponge layer 20 along the longitudinal direction of the core member 10, a variation thereof along the circumferential direction, arrangement of a projection(s) on an inner face of the sponge layer 20, and the like, pressure to the core member 10 from the peripheral face can be fluctuated so that stimulations to a penis can be changed and increased.

In a sectional view of FIG. 3, the core member 10 is covered with the sponge layer 20 caused to extend up to the distal end portion of the core member 10, but a range of the core member covered with the sponge layer 20 is restricted to a portion except for the distal end portion of the core member 10, and a sponge member (a bottom portion sponge layer) 30 which is a separate member is additionally provided for the distal end portion of the core member 10 in an example of FIG. 4.

In both the examples, since a sponge material compressed elastically is disposed between the distal end portion of the core member 10 and the inner bottom face of the container main unit 3, it is possible to accommodate long and short penis lengths. That is, when a penis length is shorter than a standard length, the sponge positioned at the distal end side of the core member 10 receives the distal end of the core member to prevent collapse and deformation of a distal end shape of the core member and maintains a rubbing force to a penis distal end, while, when the penis length is longer than the standard length, the sponge positioned at the distal end side of the core member 10 is compressed and deformed by the penis distal end to be capable of maintaining a rubbing force between the distal end of the core member and the penis distal end sufficiently.

In the present embodiment, an example that diameters of the both end portions of the container 2 in the longitudinal direction are approximately equal to each other has been shown, but it is preferable that an end portion of the container main unit 3 on the depth side is formed to be smaller in outer diameter than an end portion thereof on the opening portion side in order to increase stimulations to the penis distal end from rubbing.

Figure 6:
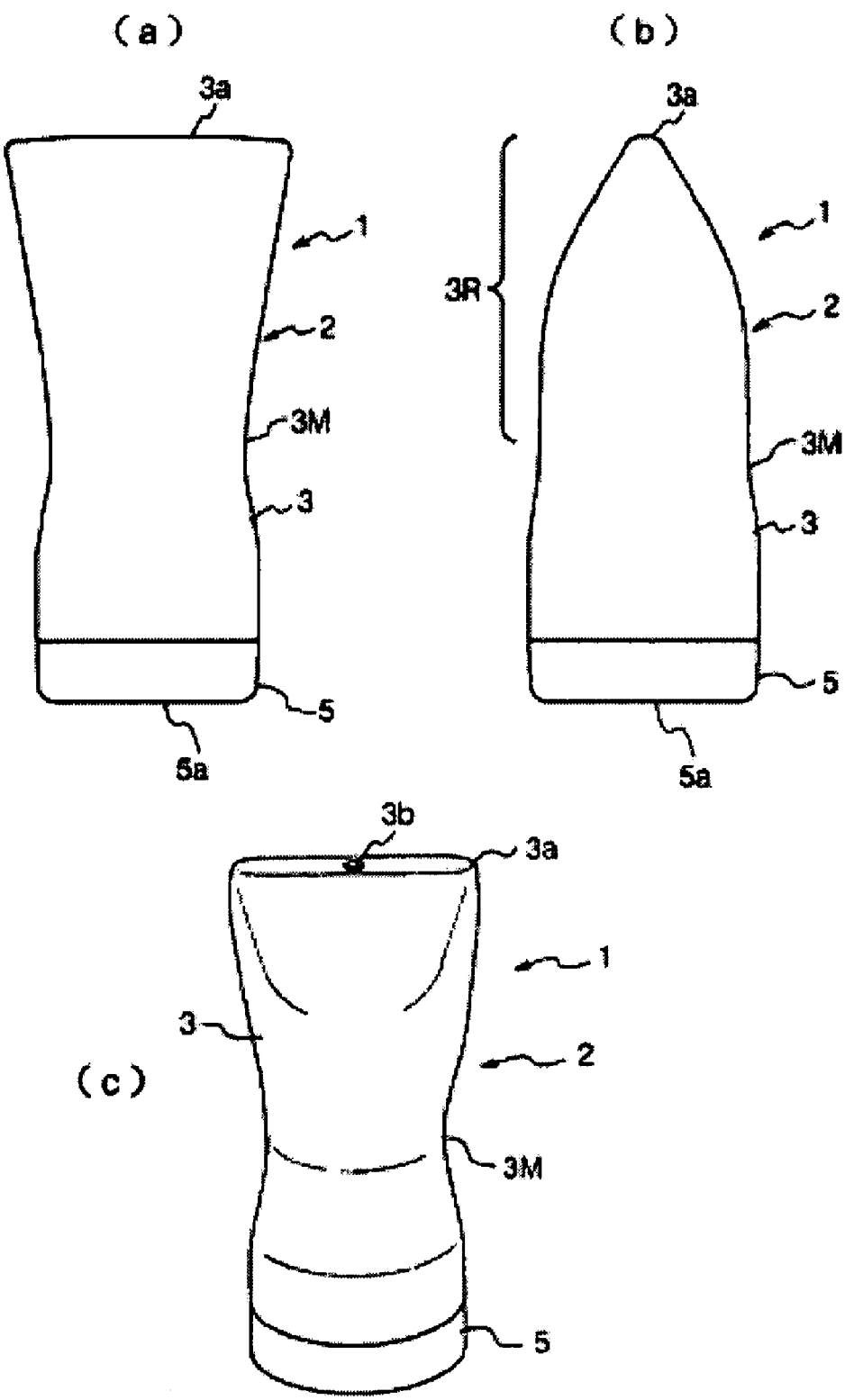
FIGS. 6(a), 6(b) and 6(c) are a front view, a side view, and a perspective view showing a configuration of a sperm collecting apparatus according to a second embodiment of the present invention.
Figure 7:
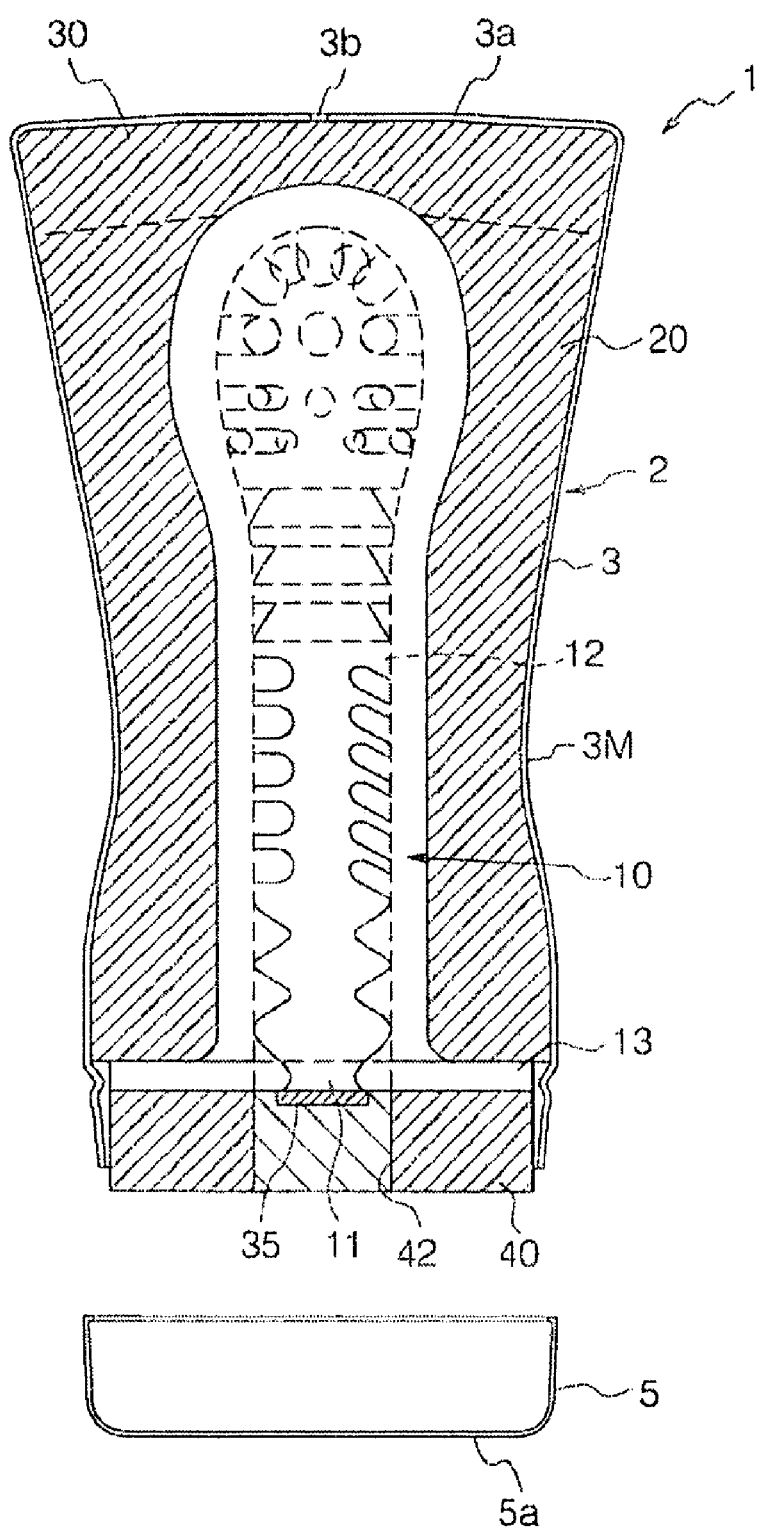
FIG. 7 is a vertical sectional view of the sperm collecting apparatus.
Figure 8:
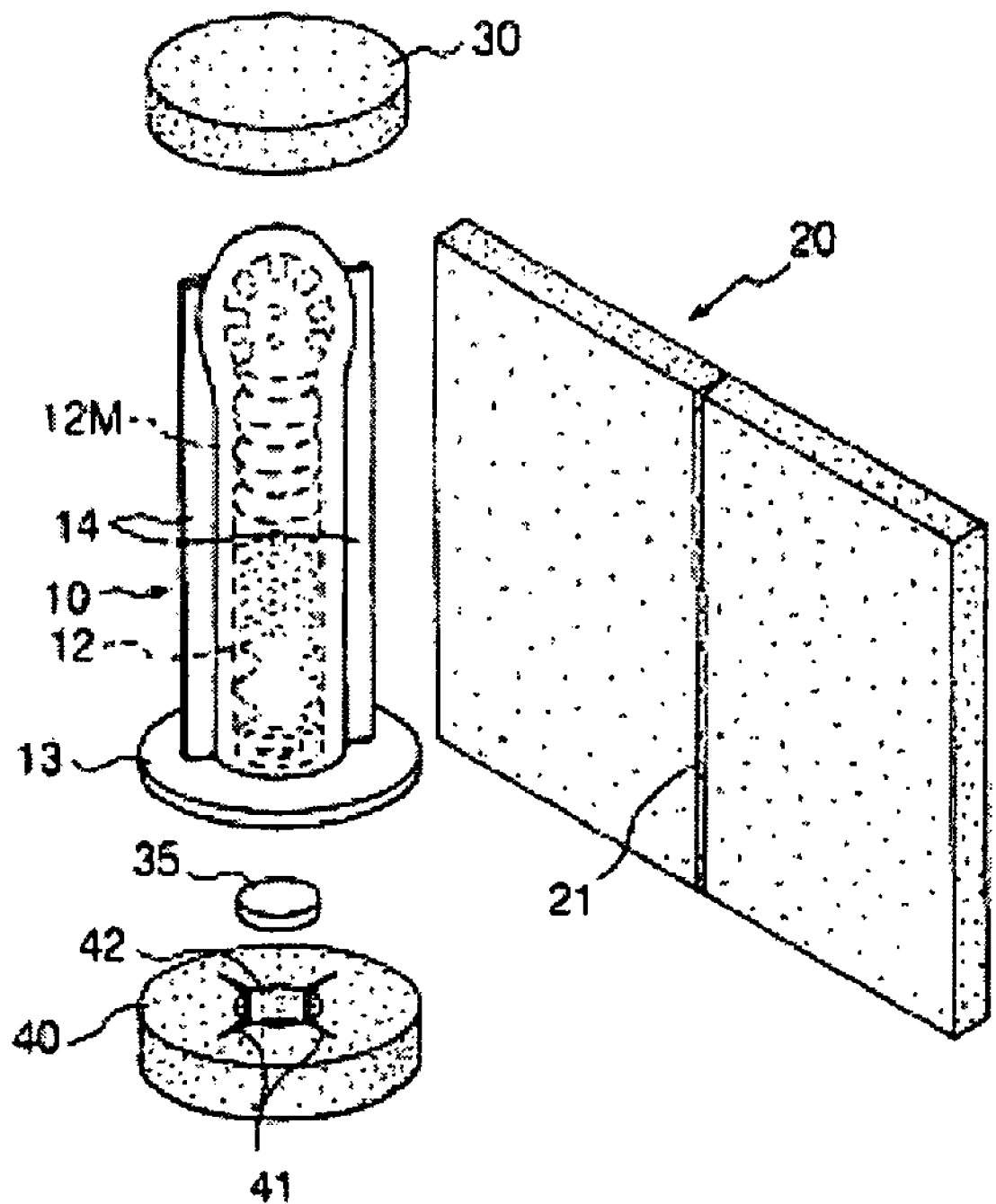
FIG. 8 is an exploded perspective view of constituent elements.

That is, FIGS. 6(a), 6(b) and 6(c) are a front view, a side view, and a perspective view showing a configuration of a sperm collecting apparatus according to a second embodiment of the present invention, FIG. 7 is a vertical sectional view of the sperm collecting apparatus, and FIG. 8 is an exploded perspective view of respective constituent elements.

The most different point between the sperm collecting apparatus 1 according to this embodiment and the sperm collecting apparatus according to the above first embodiment lies in a shape of the container. The containers of the respective embodiments are the same in a point that the both are formed in non-cylindrical shape, but the container according to this embodiment is different from that according to the first embodiment in a point that the former container is formed in a circular shape at one end face thereof in the longitudinal direction while a width of a side face shape thereof gradually decreases toward the other end side thereof so that a width of the other end thereof becomes the minimum.

That is, the sperm collecting apparatus 1 includes a container 2 having a non-cylindrical container main unit 3 whose one end face in a longitudinal direction thereof is opened in a circular shape and a cap 5 that is attached to and detached from an opening portion 4 of the container main unit 3 to open and close the opening portion, a core member 10 made from gel-like resin, that is accommodated in the container main unit 3 and has an insertion room 12 extending to an inner portion of the core member from an insertion port 11 at one end face in a longitudinal direction therein, and a sponge layer 20 that is interposed between the core member 10 made from gel-like resin and an inner wall of the container main unit.

Further, the sperm collecting apparatus 1 includes a sponge member (a bottom sponge layer) 30 disposed on an inner bottom face of the container main unit 3, a lid plate 35 additionally provided at the insertion port 11 of the core member 10 to close the same, and a sponge lid 40 additionally provided on an end face of the core member 10 on an insertion side and tightly contacts with the inner wall of the container main unit to perform such a function as positioning of the core member 10 or fixing thereof.

The container main unit 3 is made from a resin material with a required thickness. A width of the container main unit is the maximum at one end portion (an end portion at the insertion side) in the longitudinal direction, where the width of the container main unit decreases from the one end portion toward a necked portion in an intermediate portion 3M, further slightly gradually increases toward the other end and gradually decreases, and it becomes the minimum at the other end portion 3a, as shown in a side view of FIG. 6(b). The width of the other end portion is larger than that of the insertion side end portion in a front view of FIG. 6(a).

The maximum feature of the container main unit 3 lies in that, since the widths of the intermediate portion 3M and the depth portion 3R are reduced and the container main unit is formed to be elastically deformable, the depth portion 3R can be pressurized with desirable load by a user's finger when he performs a rubbing operation to his penis while holding the container main unit with his one hand. Therefore, he can apply desired stimulations and oppressive feelings to his penis at an arbitrary timing and even if air enters between the inner wall of the core member and a penis, the air can be degassed naturally since he conducts a reciprocating operation while squeezing the container main unit with his finger tips. Alternatively, by preliminarily compressing the depth portion 3R with his fingers before inserting his penis in the core member, he can insert his penis into the core member after eliminating a room in which air enters (remains).

Further, this embodiment has such a feature that a position where the narrow portion of the depth portion 3R abuts on the penis distal end (glans of penis) can be changed by only rotating a positional relationship of the container main unit 3 to the penis by only 90 degrees. That is, since the distal end portion of the container main unit according to this embodiment is reduced in the width in a taper shape, which is different from a simple cylindrical container main unit, a position where an inner wall of the narrowed portion of the depth portion 3R stimulates the penis distal end is changed by changing an angle of the entire apparatus in a rotating direction so that variations in the rubbing operation can be secured.

Since the sperm collecting apparatus of this type can produce any proper stimulation suitable for a user who does not wish for strong sexual stimulations, such as an elderly person or a disabled person, its utility becomes high. That is, it is possible that a user can gain the sense of satisfaction suitable for the user himself by adjusting the strength of stimulations.

While a user is compressing the depth portion 3R to squeeze out semen and to accumulate the same in the deepest portion of the core member after ejaculation into the core member utilizing the fact that the depth portion 3R is elastically deformable, he can pull out his penis so that cleanness can be maintained.

Next, this embodiment is similar to the first embodiment in a point that a drawback such that lubricating liquid inside the inlet side runs dry can be prevented by flattening the upper face 5a of the cap 5 and placing the container upright such that the insertion port 11 side of the core member faces downwardly. A configuration where the insertion port 11 is closed using the lid plate 35 is similar to that in the first embodiment. In this case, the lid plate 35 can be fitted in the hole 42 provided on the sponge lid 40.

The core member 10 is a bag-like member made from gel-like resin with viscosity such as elastomer or gel-like rubber like the first embodiment, it includes a large-diameter flange 13 on end face at its insertion side and an insertion room 12 with a diameter larger than that of the insertion port 11 is formed inside a small diameter insertion port 11 so as to communicate with the insertion port 11. A projection(s) or a fold(s) is formed in the insertion room 12 with a proper arrangement. A proper amount of lotion or the like serving as lubricating liquid is preliminarily charged in the insertion room 12.

By making an inner diameter of a portion 12M of the insertion room 12 of the core member corresponding to the small-diameter portion 3M provided in the intermediate portion of the container main unit 3 in the longitudinal direction smaller than those of the other portions thereof, pressure to a penis is fluctuated during a rubbing operation so that stimulations applied to the penis can be fluctuated/increased. A point that, since the intermediate portion of the core member 10 in the longitudinal direction is always pressed by the small-diameter portion 3M of the container main unit 3, a shape-holding force of the core member 10 is increased and buckling of the core member at a time of forcible insertion or rubbing of a penis is prevented is similar to the first embodiment.

Plate-like ribs 14 extending in an axial direction are also integrally formed on an outer peripheral face of the core member 10. The ribs 14 can be ribs extending in a circumferential direction.

A point that a small cut line 15 for degassing serving as a check valve is cutting-formed at a proper point in the distal end portion of the core member 10 is similar to the first embodiment.

Also, as shown in FIG. 7, by causing one portion of the sponge lid 40 to project beyond the end edge of the opening portion of the container main unit 3 to the outside by a predetermined amount (for example, 3 mm to 5 mm), a drawback such that due to repetitive abutting of an opening portion peripheral edge of the container main unit 3 on a proximal portion of user's penis or skin around his penis during use of the container main unit 3, a portion of the user on which the opening portion peripheral edge abuts is injured or the user feels discomfort about the use can be eliminated.

Furthermore, by fitting a fitting member made from sponge (urethane foam) in the hole 42 to close the hole 42 in advance, the fitting member can be pushed into the insertion room at a time of penis insertion. In this case, the fitting member rolls between a penis distal end and the insertion recess inner wall so that the penis can be imparted with irregular stimulations.

Next, a configuration of the sponge layer 20 is similar to that in the first embodiment, and it includes a holding portion 21 that holds a rib 14 formed on an outer periphery of the core member to prevent buckling of the core member 10.

Next, FIGS. 9(a), 9(b) and 9(c) are a configuration diagram of an inner cap used in a sperm collecting apparatus according to another embodiment of the present invention, a vertical sectional view of main parts showing a state before the inner cap is attached, and a vertical sectional view of the main parts showing a state after the inner cap has been attached. Like portions as those in the sperm collecting apparatus according to the respective embodiments described above are attached with like reference numerals in the following explanation.

The sperm collecting apparatus 1 according to this embodiment includes an inner cap 50 having a projecting portion 51 that is fitted to an insertion port 11 provided in a front end face of the core member 10 from the outside to close the insertion port 11 and a supporting face (a supporting plate) 52 that supports the projecting portion 51 and contacts with one end face (a front end face) of the core member 10 in a longitudinal direction thereof. The inner cap 50 is formed of, for example, a resin plate (a material harder than a constituent material for the core member or the sponge) thinner than the container main unit 3, and the projecting portion 51 is pressure-fitted into the insertion port 11 so that the projecting portion 51 is caused to tightly contact with an inner peripheral face of the insertion port 11 to prevent leakage of lotion inside the core member. Since the projecting portion 51 is harder than a constituent material for the core member 10, it tightly contacts with and is fitted into the insertion port 11 to be capable of preventing leakage of lotion, and attaching and detaching operations to and from the insertion port 11 can be performed smoothly. The supporting face 52 expanding from an outer peripheral edge of the projecting portion 51 in an outer diametrical direction tightly contacts with at least one portion of the front end face of the core member 10 to serve to prevent spread or outflow of lotion in the outer diametrical direction even if the lotion leaks. Since an outer peripheral edge of the supporting face 52 tightly contacts with (or is preliminarily integrated with) an inner peripheral face of the cap 5, the whole inner cap 50 is pressure-contacted with the front end face of the core member 10, when the cap 5 is closed, so that positional deviation is prevented and lotion leakage does not occur.

An annular recess 52a is provided on the supporting face 52 of the inner cap 50 and a recess 13A is provided on the front end face (flange portion) 13 of the core member 10 that the recess 52a faces, so that lotion for insertion is held in a room formed between both the recesses 52a and 13A. By adopting this configuration, a state that a sufficient amount of lotion has adhered on an outside peripheral face of the insertion port 11 can be secured when the inner cap 50 is detached prior to use start. Therefore, when a user inserts his penis, he can perform smooth insertion without feeling any discomfort. On the other hand, the lotion for insertion can be retained in a space formed between the recesses 52a and 13A without leakage at a closing time of the cap 5. Accordingly, the lotion is prevented from leaking from the front end face of the core member 10 and drying during transportation and display.

On the other hand, the insertion port is conventionally capped by causing disk-like urethane foam including an X-shaped cut at a central portion thereof to abut on the front end face of the core member, but since sealing obtained by the cutting is insufficient, such a problem as leakage of lotion during use or dry (occurrence of pain at a time of penis insertion) due to leakage of lotion during transportation or display arises.

According to the present embodiment, these drawbacks can be eliminated once for all. Particularly, since no urethane is present on the insertion port side, a user does not feel textured discomfort at his insertion and feels smooth and comfortable.

The configuration of the space for retaining the lotion for insertion can be applied to the other all embodiments (including respective embodiments of the second invention and the third invention) of a type of using the inner cap.

Figure 10:
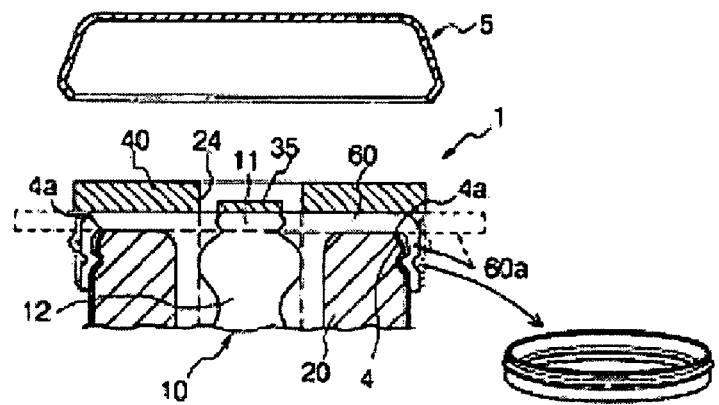
FIG. 10 is a sectional view showing a configuration of a sperm collecting apparatus according to another embodiment of the present invention.

Next, FIG. 10 is a sectional view showing a configuration of a sperm collecting apparatus according to another embodiment of the first invention. In the sperm collecting apparatus according to this embodiment, a disk-like flange portion 60 is formed on one end face of the core member 10 in a longitudinal direction (an axial direction), an outer peripheral edge 60a of the flange portion 60 made from a soft material is formed to have a large diameter so as to bulge beyond the opening portion 4 of the container main unit 3 in an outer diametrical direction, and an end edge 4a of the opening portion 4 of the container main unit is covered with the outer peripheral edge 60a of the flange portion 60 made from a soft material so that the outer peripheral edge 60a of the flange portion 60 is held in a state that it has been folded outside the opening portion 4 such that a portion of a human body does not contact with the end edge 4a directly. The folded outer peripheral edge 60a can be maintained in a state thereof tightly contacting with the end edge 4a by an elastic force of the outer peripheral edge 60a itself or it can be bonded to the outer face of the opening portion 4 in a state that the outer peripheral edge 60a of the flange portion 60 has been pushed back to the outside of the opening portion 4. Alternatively, an outside of the outer peripheral edge 60a folded back can be pressed by an annular pressing member shown in FIG. 10.

With this configuration, when a user detaches the cap 5 to expose the front end face of the core member 10 and inserts his penis into the insertion port 11 to conduct a rubbing operation, he is prevented from feeling pain due to contact of the end edge 4a of the opening portion 4 with his lower abdomen. The outer peripheral edge 60a is prevented from being peeled off during use by bonding the outer peripheral edge 60a of the folded flange portion to the outer face of the opening portion 4 in advance.

Figure 9:
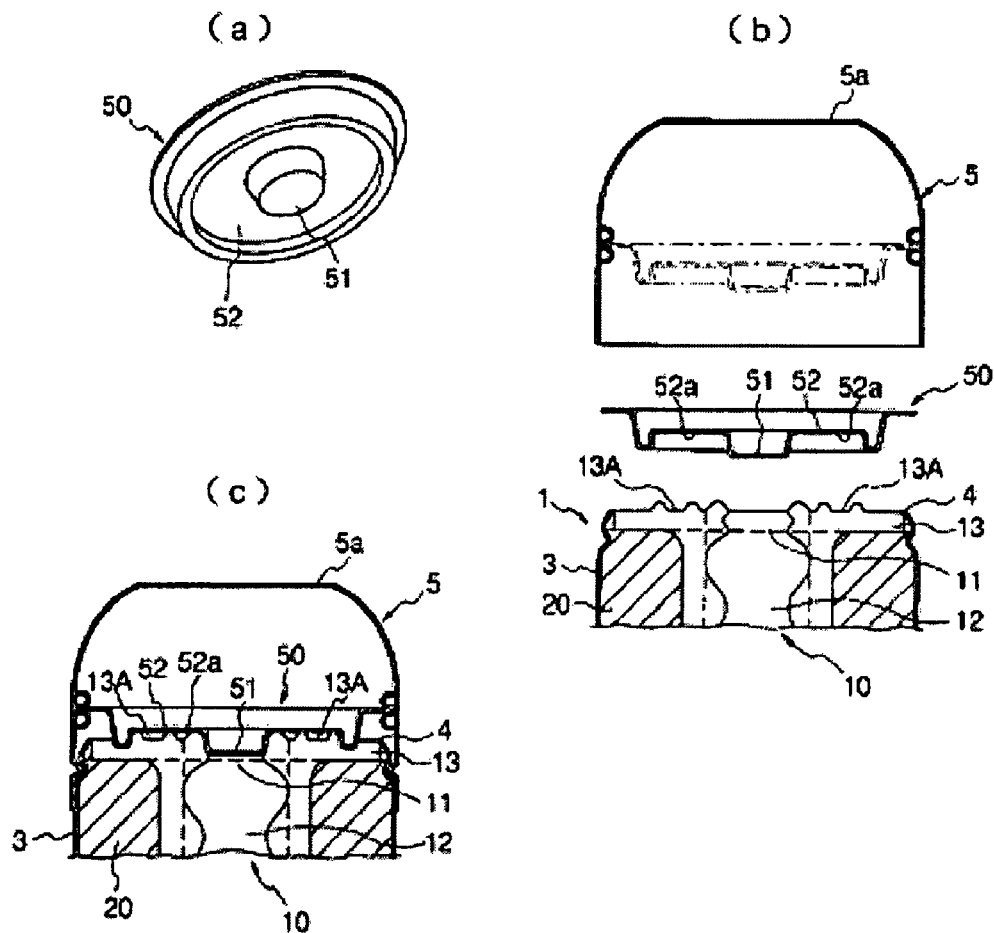
FIGS. 9(a), 9(b) and 9(c) are a configuration diagram of an inner cap used in a sperm collecting apparatus according to another embodiment of the present invention, a vertical sectional view of main parts showing a state before the inner cap is attached, and a vertical sectional view of the main parts showing a state after the inner cap has been attached.

The inner cap 50 shown in the embodiment shown in FIG. 9 can be applied to the embodiment shown in FIG. 10.

Next, the second invention will be explained in detail by embodiments shown in the drawings.

Figure 11:
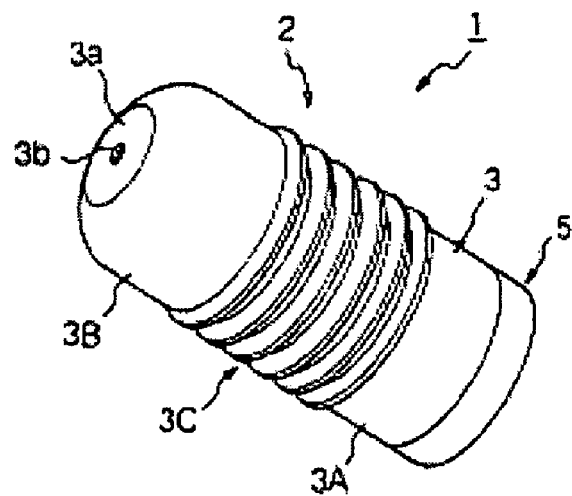
FIG. 11 is an appearance perspective view of a sperm collecting apparatus according to a first embodiment of the second invention.
Figure 12:
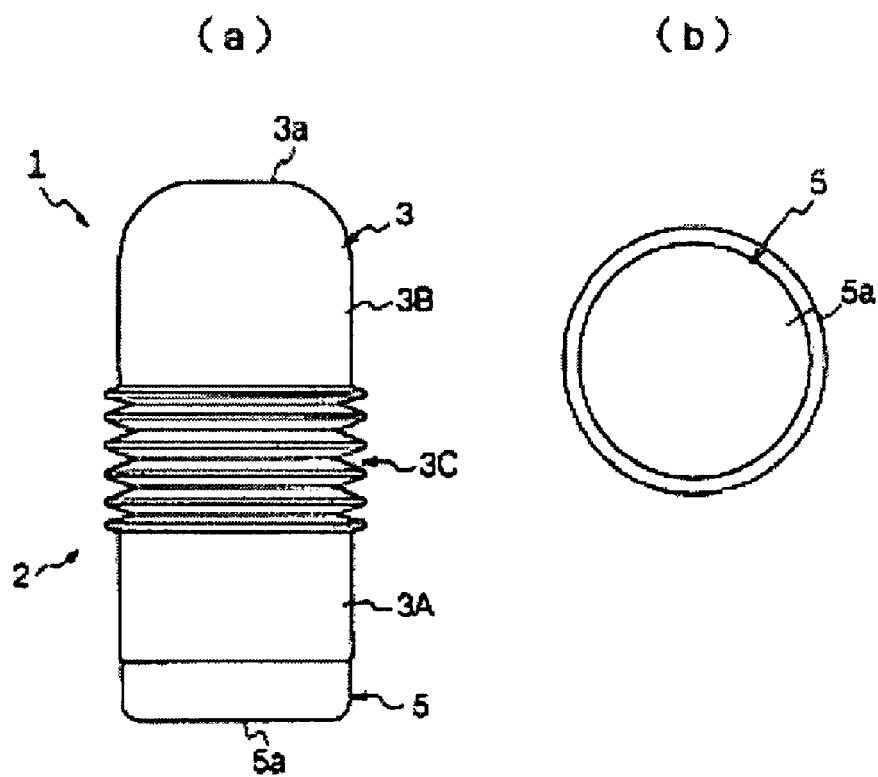
FIGS. 12(a) and 12(b) are a front view and a bottom view of the sperm collecting apparatus.
Figure 13:
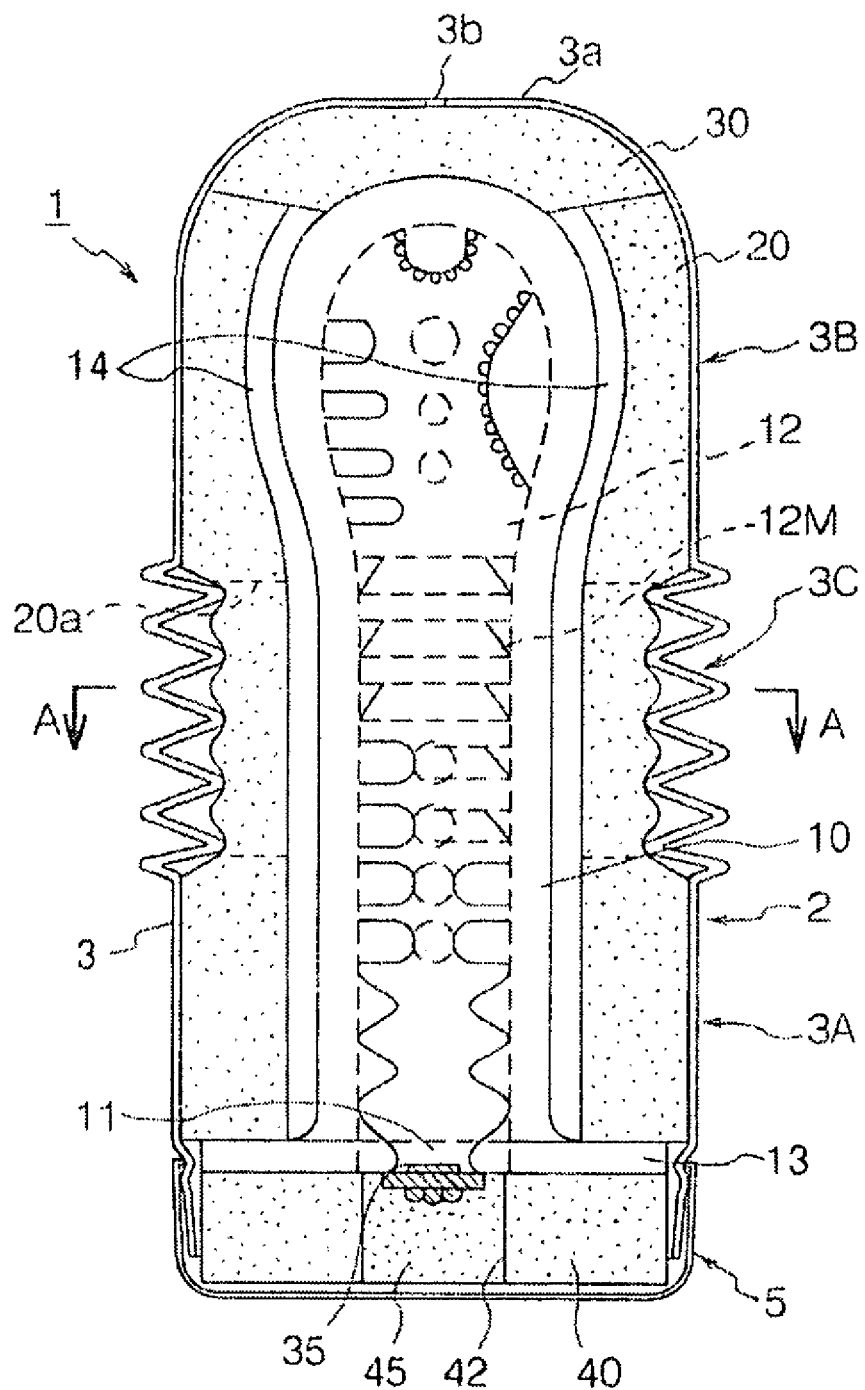
FIG. 13 is a vertical sectional view of the sperm collecting apparatus.
Figure 14:
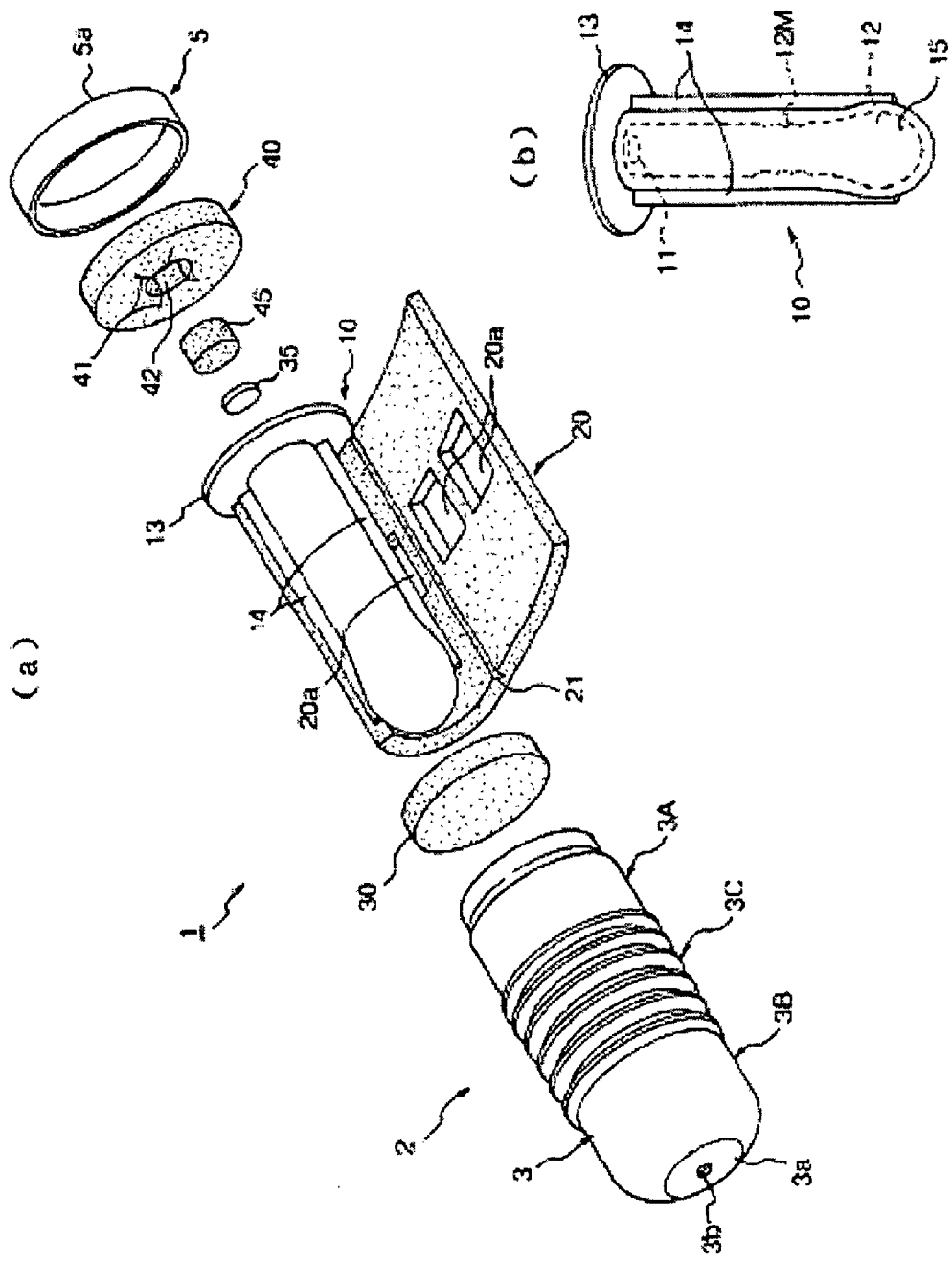
FIGS. 14(a) and 14(b) are an exploded perspective view of respective constituent elements and an appearance perspective view of a core member.
Figure 15:
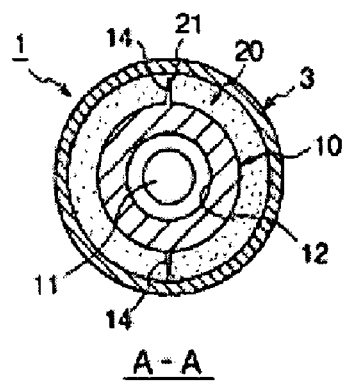
FIG. 15 is a sectional view of line A-A in FIG. 13.

FIG. 11 is an appearance perspective view of a sperm collecting apparatus according to one embodiment of the second invention, FIGS. 12(a) and 12(b) are a front view and a bottom view of the sperm collecting apparatus, FIG. 13 is a vertical sectional view of the sperm collecting apparatus, FIGS. 14(a) and 14(b) are an exploded perspective view of respective constituent elements and an appearance perspective view of a core member, and FIG. 15 is a sectional view of the sperm collecting apparatus taken along line A-A in FIG. 13.

The sperm collecting apparatus 1 includes a container 2 having a non-cylindrical container main unit 3 whose one end face in a longitudinal direction thereof is opened and a cap 5 that is attached to and detached from an opening portion 4 of the container main unit 3 to open and close the opening portion, a core member 10 made from a gel-like resin, that is accommodated in the container main unit 3 and has an insertion room 12 extending to an inner portion of the core member from an insertion port 11 at one end face in a longitudinal direction therein, and a sponge layer 20 that is interposed between the core member 10 made from a gel-like resin and an inner wall of the container main unit 3.

The sperm collecting apparatus 1 includes a sponge member (a bottom sponge layer) 30 disposed on an inner bottom face of the container main unit, a lid plate 35 additionally provided at the insertion port 11 of the core member to close the same, and a sponge lid 40 additionally provided on an end face of the core member 10 at an insertion side and tightly contacting with the inner wall of the container main unit to perform such a function as positioning of the core member 10 or fixing thereof.

The container main unit 3 is formed from a resin material with a desired thickness, and an intermediate portion 3C thereof in a longitudinal direction is an easily deformable portion that is more deformable than both end portions 3A and 3B of the container main unit 3 in the longitudinal direction (an axial direction).

The easily deformable portion 3C is a portion that supports one end portion 3B of the container 2 to be capable of swinging (tilting or rotating) to the other end portion 3A of the container 2 in the longitudinal direction or supports the one end portion 3B to be capable of expanding and contracting in the longitudinal direction.

In this embodiment, since the easily deformable portion 3C is an accordion-shaped portion, a distance between both the end portions 3A and 3B in the longitudinal direction can be freely decreased and increased according to expansion and contraction of the accordion-shaped portion and swinging in a direction crossing (orthogonal to) the longitudinal direction can be conducted. Specifically, the term "swinging" is a concept including all tilting in front and rear, and left and right directions, tilting in another lateral direction, movement in a rotating direction, and movement in a twisting direction.

As the configuration of the easily deformable portion 3C except for the accordion-shaped portion, such a method as thinning of the thickness of the intermediate portion to make elastic deformation easy (a thin portion) or using an elastically-deformable material (soft material) as a material for the intermediate portion is considered.

The intermediate portion can be formed to be capable of expanding and contracting or swinging by forming the intermediate portion in a mesh configuration or arranging a fine undulation portion or fine groove portion in the intermediate portion.

An upper face 5a of a cap 5 made from a resin material similar to a material for the container main unit 3 is formed in a flat face suitable for stationary placement on a flat place, and an end portion 3a of the container main unit 3 opposed to the opening portion 4 is formed in an arc shape (a spherical face) that is not suitable for stationary placement. Therefore, the container main unit 3 closed by the cap 5 can be placed upright on a flat place such that the upper face 5a of the cap 5 faces downwardly. On the other hand, since it is difficult to stationarily place the other end portion 3a of the container main unit on a flat place stably, a drawback that lubricating liquid accumulates in the depth portion of the insertion room 12 in an unused state so that lubricating liquid on the inlet side runs dry is eliminated.

A small hole 3b for degassing is preliminarily formed at the other end 3a of the container main unit as necessary and it is preliminarily sealed in the unused state by a seal (not shown). The seal is removed when it is used and a tight contact degree or a tight contact feeling between the inner wall of the core member and a penis can be adjusted by opening and closing the small hole 3b during use with a user's finger. That is, since the penis tightly contacts with the inner wall of the core member in a closed state of the small hole 3b, a tightening force becomes strong, while the tightening force becomes weak in a state that the small hole 3b is opened. It is made possible to change the tightening force and to change stimulations according to a simple operation such as only opening and closing the small hole. When a user feels pain in his penis, he can open the small hole.

The core member 10 is a bag-like member made from gel-like resin with viscosity such as elastomer or gel-like silicon resin or gel-like rubber, it includes a large-diameter flange 13 at an end face on the insertions side, and the insertion room 12 with a diameter larger than the insertion port is formed so as to communicate with the small-diameter insertion port 11. A projection(s), a fold(s), or the like is formed in the insertion room 12 with a proper arrangement. A proper amount of the lotion or the like serving as lubricating liquid is preliminarily charged in the insertion room 12.

Regarding an inner diameter of the insertion room 12 of the core member 10, an inner diameter of a portion 12M corresponding to the easily deformable portion 3C provided in the intermediate portion of the container main unit 3 in the longitudinal direction is narrower than inner diameters of the other portions. Therefore, when a penis is forcibly inserted from the insertion port 11 into the insertion room 12, of course, a distal end of the penis repeatedly passes through the narrowed portion during rubbing action, so that pressure to the penis fluctuates, which can result in fluctuation and increase of applied stimulations. Since the intermediate portion of the core member 10 in the longitudinal direction is always pressed by the inner diameter portion of the accordion portion configuring the easily deformable portion 3C of the container main unit, a shape-holding force of the core member is raised, so that buckling of the core member is prevented at a time of forcible insertion and rubbing of a penis.

By making the inner diameter (tightening force) of the insertion room 12 on the inlet side smaller than the inner diameter of the inner depth portion and clamp a root portion of a penis to block useless floating movement, stimulations can be concentrated to the glans of penis.

Plate-like ribs 14 extending in an axial direction are also integrally formed on an outer peripheral face of the core member 10. The ribs 14 can be ribs extending in a circumferential direction.

A short cut line 15 for degassing serving as a check valve is formed by cutting at a proper point on a distal end portion of the core member 10 in advance. Since the cut line 15 is completely closed in a non-insertion state of a penis according to an elastic force of the core member itself, lubricating liquid inside the core member is prevented from leaking and when an internal pressure is raised due to penis insertion, the air that tends to be accumulated between a penis distal end and an inner bottom face of the insertion room 12 can be degassed by opening the cut line 15. After the air is removed, even if an operation for rubbing of the penis is performed, the cut line 15 continues to close so that the amount of lubricating liquid hardly flowing to the outside can be suppressed to such an amount that use of the apparatus is not disturbed. However, even if a small amount of lubrication liquid leaks from the cut line 15, there will not be such a state that lubricating liquid inside the core member lacks to such an extent that the shortage disturbs use of this apparatus.

By arranging a lid plate 35 that tightly contacts with an end face of the core member 10 around a peripheral edge of the insertion port 11 to openably/closably close the insertion port at the insertion port 11 of the core member to close the insertion port, lubricating liquid charged in the insertion room 12 is prevented from leaking. Accordingly, even when the container 2 is placed such that the cap 5 side faces downwardly, lubricating liquid does not leak, so that the insertion port side of the insertion room 12 can be maintained in sufficiently-lubricated state. Reduction of lubricating liquid inside the core member due to drying is prevented owing to presence of the lid plate 35. Drying inside the core member is further prevented by impregnation of lubricating liquid in the sponge lid 40. Since the lid plate 35 is made from gel-like resin similar to the material for the core member 10, it can tightly contact with the insertion side end face of the core member to seal the insertion port 11. On the other hand, when a penis is inserted to the insertion port, the lid plate is pushed into the insertion port by a penis distal end, and it does not disturb a rubbing operation performed thereafter. On the contrary, since rubbing is conducted in a state that the lid plate 35 is interposed between the penis distal end and the inner depth portion of the insertion room, irregular stimulations can be obtained.

A cut line 41 for penis insertion is formed in the sponge lid 40 additionally provided on a face of the flange 13 of the core member in advance, but when the insertion port 11 is closed from the outside using the lid plate 35, a through-hole or a recess 42 fitted with the lid 35 can be formed at a central portion of the sponge lid 40 in advance. Thereby, an inside face of the sponge lid 40 can be caused to tightly contact with the face of the flange 13, so that a force for positioning and fixing the core member 10 increases owing to the sponge lid 40. The force for fixing the lid plate 35 increases.

A fitting member 45 that closes the through-hole 42 formed at the central portion of the sponge lid 40 is fitted into the through-hole 42, so that the fitting member 45 can be caused to fall off from the through-hole 42 and is moved from the insertion port 11 into the insertion room 12 by a pressing force applied when a user inserts his penis from the opening portion side of the container main unit 3. As the fitting member 45, any material such as a small block made from a sponge material such as urethane can be used. The fitting member 45 that has been pushed into the depth portion in the insertion room 12 by the penis can abut on the glans of penis to impart irregular stimulations thereto during a rubbing operation to the penis.

When the sponge lid 40 having the cut line 41 is interposed between the end face of the core member 10 at the insertion port side and the cap 5, as also shown in FIG. 13, a portion of the sponge lid 40 is caused to project beyond the end edge of the opening portion of the container main unit 3 to the outside by a predetermined amount (for example, 3 mm to 5 mm). By adopting this configuration, a drawback such that due to repetitive abutting of an opening portion peripheral edge of the container main unit 3 on a proximal portion of user's penis or skin around his penis during use of the container main unit 3, a portion of the user on which the opening portion peripheral edge abuts is injured or the user feels discomfort about the use can be eliminated.

Next, the sponge layer 20 is made of a foam resin sheet but is not a simple sheet, and is formed with a holding portion 21 holding a rib 14 formed on the outer periphery of the core member to prevent buckling of the core member. In this embodiment, an example that two plate-like ribs 14 extending in an axial direction are provided is shown, where in order to hold these ribs 14, the core member 10 and the sponge layer 20 are integrated by providing the holding portion 21 formed as a cut line extending in the axial direction in an intermediate portion of the sponge layer 20 in a circumferential direction to hold one rib 14 in the holding portion 21 and holding the other rib 14 between both end faces of the sponge layer 20 in the circumferential direction and the integrated core member 10 and sponge member 20 are inserted into the container main unit 3 from the opening portion 4 side (FIG. 15).

When there are three or more ribs 14, the number of holding portions 21 is increased correspondingly. When a forming direction of the rib 14 is a circumferential direction or another direction, a forming direction of the holding portion is changed similarly.

Based on such a contraption as variation of the thickness of the sponge layer 20 along the longitudinal direction, and a variation thereof along the circumferential direction, and arrangement of a projection(s) on an inner face of the sponge layer 20, and the like, pressure to the core member 10 from the peripheral face can be fluctuated so that stimulations to a penis are fluctuated and increased.

By forming a plurality of small openings 20a in the sponge layer 20 facing the accordion portion along a circumferential direction at a predetermined pitch, swinging about the accordion portion can be prevented from being blocked.

In a sectional view of FIG. 13, the core member 10 is covered with the sponge layer 20 caused to extend up to the distal end portion of the core member 10, but a range of the core member covered with the sponge layer 20 is restricted to a portion except for the distal end portion of the core member 10, and a sponge member (a bottom portion sponge layer) 30 which is a separate member is additionally provided for the distal end portion of the core member in an example of FIG. 14.

In any examples, since a sponge material compressed elastically is disposed between the distal end portion of the core member and the inner bottom face of the container main unit, it is possible to accommodate long and short penis lengths. That is, when a penis length is shorter than a standard length, the sponge positioned at the distal end side of the core member receives the distal end of the core member to prevent collapse and deformation of a distal end shape of the core member and maintains a rubbing force to a penis distal end, while when the penis length is longer than the standard length, the sponge positioned at the distal end side of the core member is compressed and deformed by the penis distal end to be capable of maintaining a rubbing force between the distal end of the core member and the penis distal end.

When a user uses the sperm collecting apparatus thus configured, he detaches the cap 5 of the container 2 and pushes his penis distal end into the container 2 utilizing the cut line 41 provided in the sponge lid 40 exposed from the opening of the container main unit 3. His penis is smoothly inserted into the insertion room 12 from the insertion port 11 of the core member 10. The user holds an outer face of the container main unit 3 with his hand to conduct a piston operation along a longitudinal direction of his penis in a rubbing operation after insertion. At this time, since the other end portion 3B positioned at a distal end side beyond the easily deformable portion 3C can be swung (tilted, bent, rotated, pivoted) about the easily deformable portion 3C, a front half portion of his penis positioned inside the container main unit 3 including the glans of penis is subjected to stimulations due to varied rubbing in the inner wall of the core member 10, particularly between projecting portions or folds provided upright on the inner wall. Therefore, a sperm collecting rate can be improved.

Since the easily deformable portion 3C can be swung and can be expanded and contracted in the longitudinal direction, various operations based on a user's originality and ingenuity can be conducted, so that the sense of satisfaction can be increased and its commodity value can be improved.

When this sperm collecting apparatus is sold, a whole apparatus is sealed by a shrinkable film or the like. However, if the apparatus is displayed in a shop window with only the easily deformable portion being unsealed, a purchaser who picks up the apparatus can try its feeling of use, so that product characteristics can be widespread and buying intention thereof can be stimulated.

By providing a projecting portion upright and extending toward any direction at a position deviated from a tip portion of a glans of penis on the inner wall of the core member 10, particularly, an inner wall of the inner depth portion, stimulations caused by swinging of the distal end portion 3B can be improved.

Next, FIGS. 16(a), 16(b) and 16(c) are a perspective view of an inner cap used in a sperm collecting apparatus according to another embodiment of the second invention, a vertical sectional view of the sperm collecting apparatus before the inner cap is attached thereto, and a vertical sectional view of main parts of the sperm collecting apparatus after the inner cap has been attached thereto. Like portions as those in the sperm collecting apparatus according to the respective embodiments described above are attached with like reference numerals in the following explanation.

The sperm collecting apparatus 1 according to this embodiment includes an inner cap 50 having a projecting portion 51 that is fitted to an insertion port 11 provided in a front end face of the core member 10 from the outside to close the insertion port 11 and a supporting face (a supporting plate) 52 that supports the projecting portion 51 and contacts with one end face (a front end face) of the core member 10 in a longitudinal direction thereof. The inner cap 50 is formed of, for example, a resin plate (a material harder than a constituent material for the core member or the sponge) thinner than the container main unit 3, and the projecting portion 51 is pressure-fitted into the insertion port 11 so that the projecting portion 51 is caused to tightly contact with an inner peripheral face of the insertion port 11 to prevent leakage of lotion inside the core member 10. Since the projecting portion 51 is harder than a constituent material for the core member 10, it tightly contacts with and fitted into the insertion port 11 to be capable of preventing leakage of lotion and attaching and detaching operations to and from the insertion port 11 can be performed smoothly. The supporting face 52 expanding from an outer peripheral edge of the projecting portion 51 in an outer diametrical direction tightly contacts with at least one portion of the front end face of the core member 10 to serve to prevent spread or outflow of lotion in the outer diametrical direction even if the lotion leaks. Since an outer peripheral edge of the supporting face 52 tightly contacts with (or is preliminarily integrated with) an inner peripheral face of the cap 5, the whole inner cap 50 is pressure-contacted with the front end face of the core member 10, when the cap 52 is closed, so that positional deviation is prevented and lotion leakage is not occurred.

In this embodiment, a space serving as a pool for the lotion for insertion shown in FIG. 9 can be provided.

Figure 17:
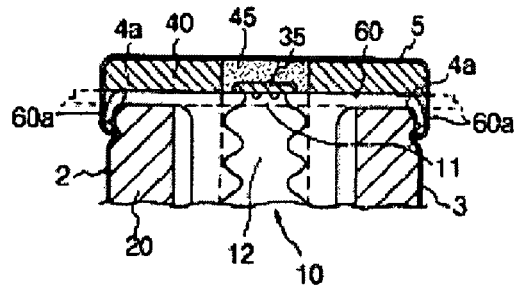
FIG. 17 is a sectional view showing a configuration of a sperm collecting apparatus according to another embodiment of the present invention.

Next, FIG. 17 is a sectional view showing a configuration of a sperm collecting apparatus according to another embodiment of the second invention. In the sperm collecting apparatus according to this embodiment, a disk-like flange portion 60 is formed on one end face of the core member 10 in a longitudinal direction (an axial direction), an outer peripheral edge 60a of the flange portion 60 made from a soft material is formed to have a large diameter so as to bulge beyond the opening portion 4 of the container main unit 3 in an outer diametrical direction, and an end edge 4a of the opening portion 4 of the container main unit 3 is covered with the outer peripheral edge 60a of the flange portion 60 made from a soft material so that the outer peripheral edge 60a of the flange portion 60 is held in a state that it has been folded outside the opening portion 4 such that a portion of a human body does not directly contact with the end edge 4a. The outer peripheral edge 60a of the flange portion 60 is preferably bonded to an outer face of the opening portion 4 in a state that the outer peripheral edge 60a has been pushed back to the outside of the opening portion 4.

With this configuration, when a user detaches the cap 5 to expose the front end face of the core member 10 and inserts his penis into the insertion port 11 to conduct a rubbing operation, he is prevented from feeling pain due to a contact of the end edge 60a of the opening portion 4 with his lower abdomen. The outer peripheral edge 60a is prevented from being peeled off during use by bonding the outer peripheral edge 60a of the folded flange portion to the outer face of the opening portion 4 in advance.

Also in this embodiment, the outer peripheral edge 60a of the flange portion 60 can be pressed by an annular pressing member such as shown in FIG. 10.

Figure 16:
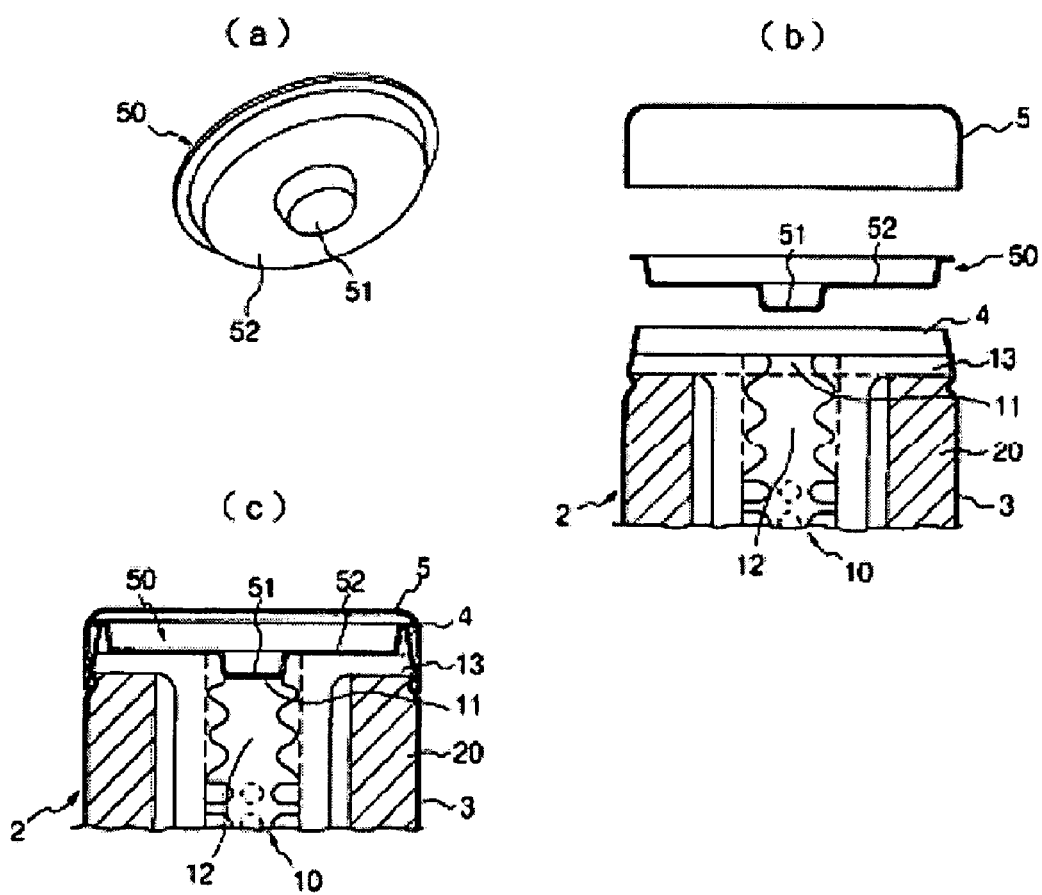
FIGS. 16(a), 16(b) and 16(c) are a perspective view of an inner cap used in a sperm collecting apparatus according to another embodiment of the present invention, a vertical sectional view before the inner cap is attached thereto, and a vertical sectional view of the main parts after the inner cap has been attached thereto.

The inner cap 50 according to the present embodiment shown in FIG. 16 can be applied to the embodiment shown in FIG. 17.

Next, a third embodiment will be explained in detail by embodiments shown in the drawings.

Figure 18:
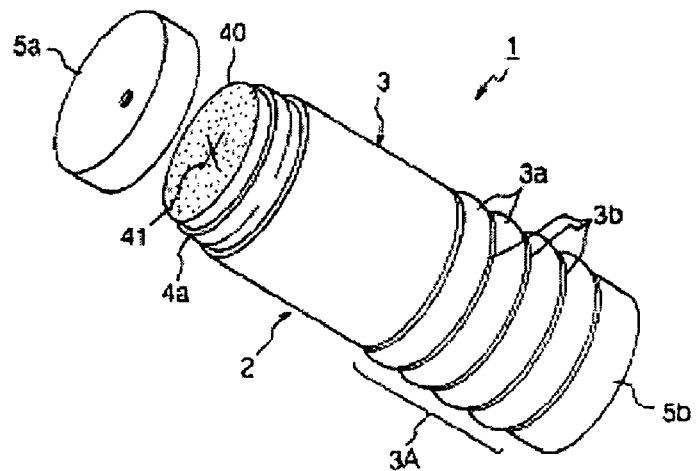
FIG. 18 is an appearance perspective view of a sperm collecting apparatus according to one embodiment of the present invention.
Figure 19:
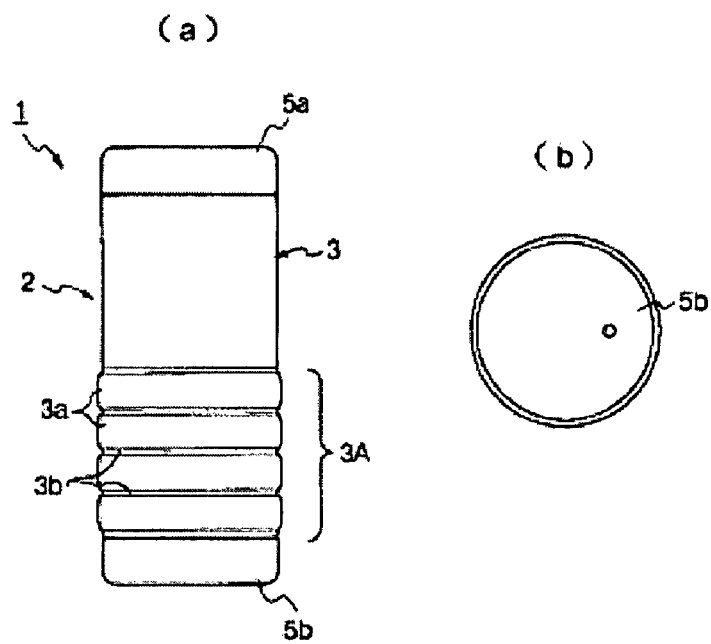
FIGS. 19(a) and 19(b) are a front view and a bottom view of the sperm collecting apparatus.
Figure 20:
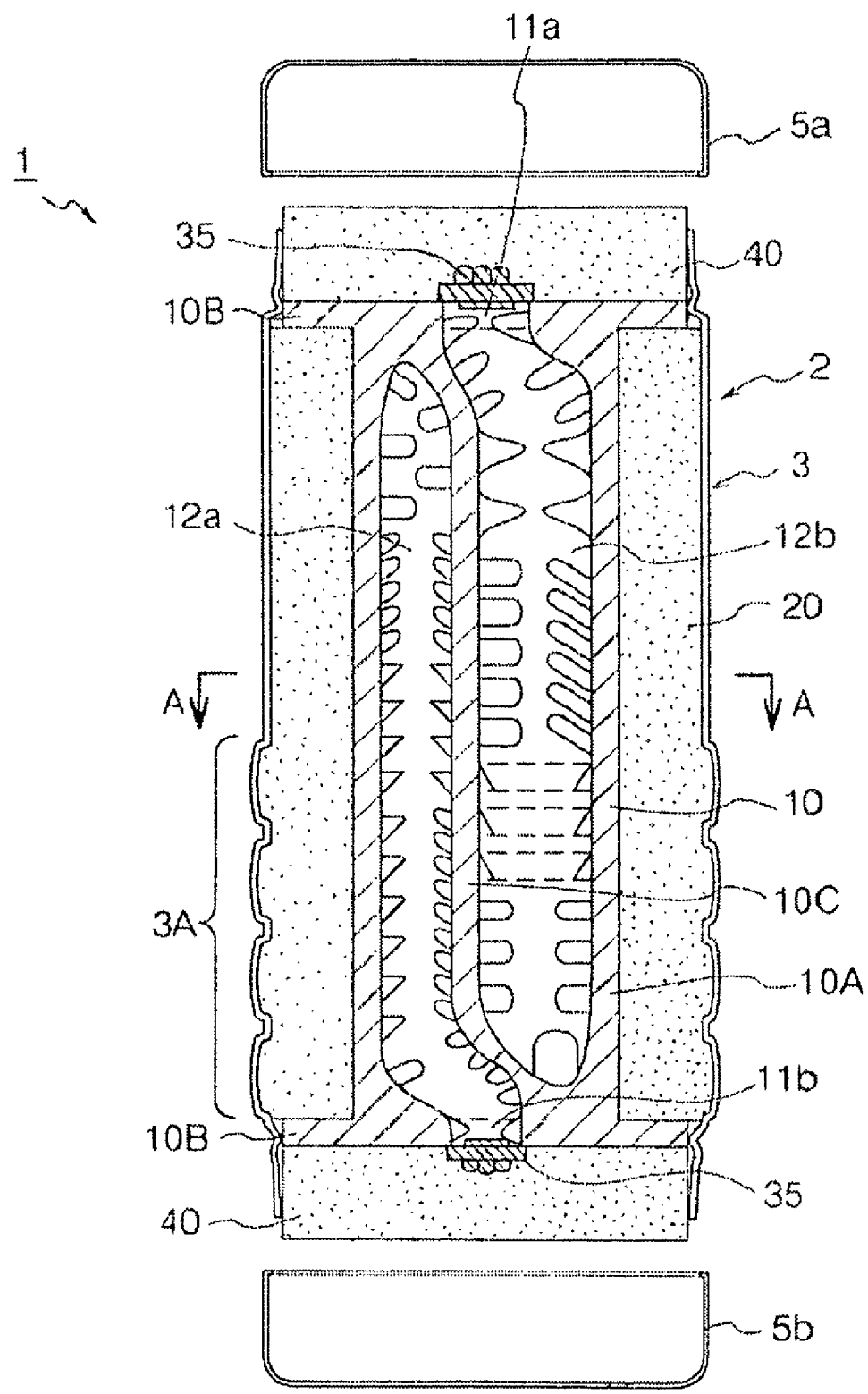
FIG. 20 is a vertical sectional view of the sperm collecting apparatus.
Figure 21:
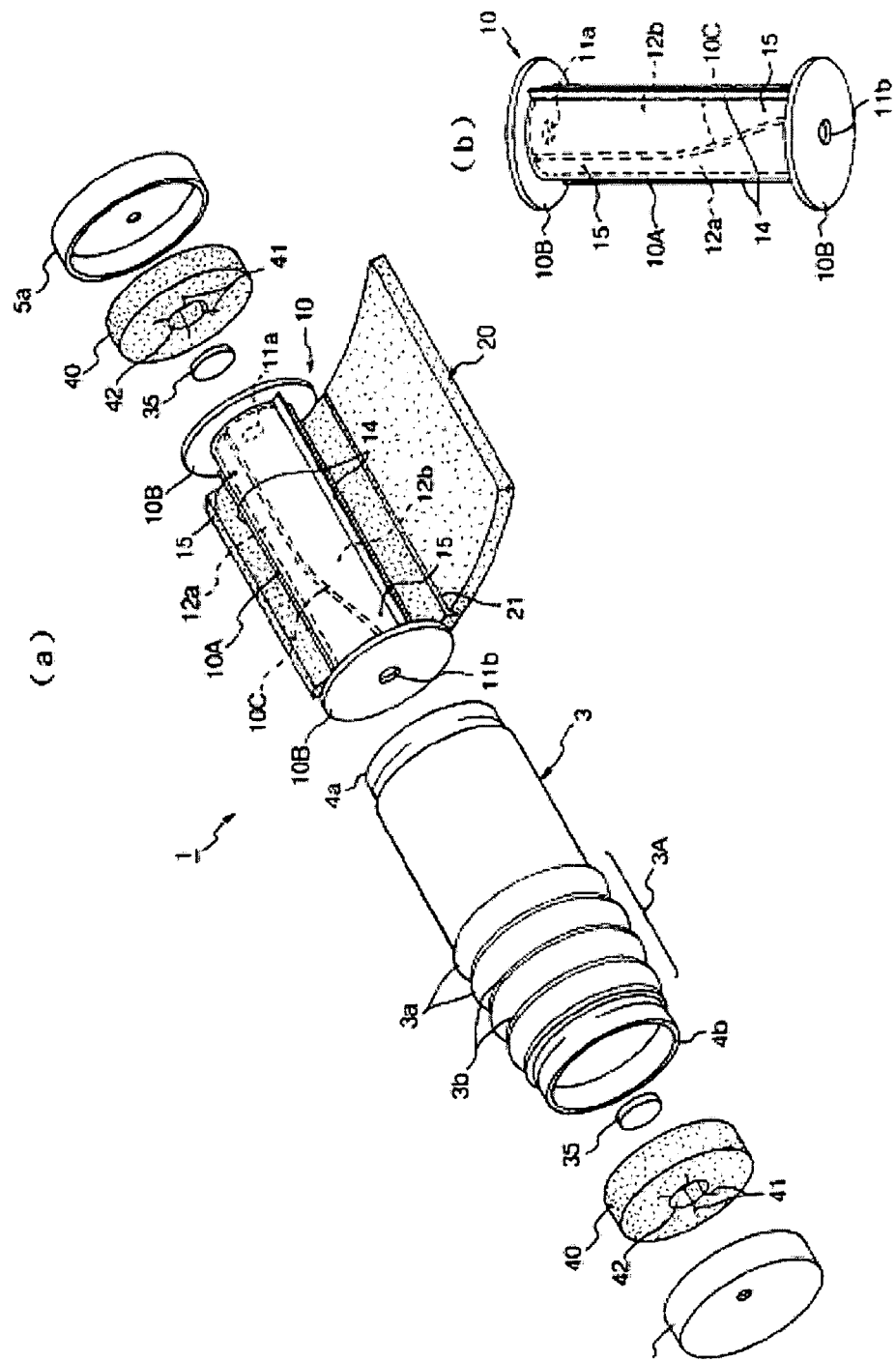
FIGS. 21(a) and 21(b) are an exploded perspective view of respective constituent elements and an appearance perspective view of a core member.
Figure 22:
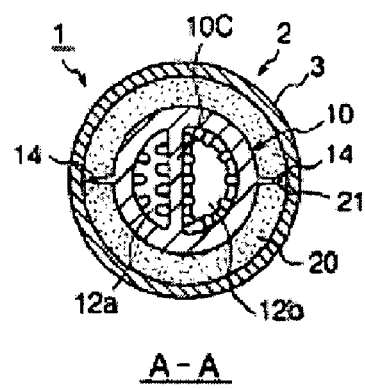
FIG. 22 is a sectional view of line A-A in FIG. 20.

FIG. 18 is an appearance perspective view of a sperm collecting apparatus according to one embodiment of the third invention, FIGS. 19(*a*) and 19(*b*) are a front view and a bottom view of the sperm collecting apparatus, FIG. 20 is a vertical sectional view of the sperm collecting apparatus, FIGS. 21(*a*) and 21(*b*) are an exploded perspective view of respective constituent elements and an appearance perspective view of a core member, and FIG. 22 is a sectional view of the sperm collecting apparatus taken along line A-A in FIG. 20.

The sperm collecting apparatus 1 includes a container 2 having a non-cylindrical container main unit 3 whose both end faces in a longitudinal direction thereof are opened and caps 5a and 5b that are respectively attached to and detached from opening portions 4a and 4b of the container main unit 3 to close and open the opening portions, a core member 10 made from a gel-like resin, that is accommodated in the container main unit 3 and has insertion rooms 12a and 12b extending to respective inner portions from insertion ports 11a and 11b at both end faces in a longitudinal direction therein, and a sponge layer 20 that is interposed between an inner peripheral face of the core member 10 and an inner wall of the container main unit 3.

The sperm collecting apparatus 1 includes lid plates 35 that are additionally attached to the respective insertion ports 11a and 11b of the core member 10 to attachably and detachably close the insertion ports 11a and 11b, and sponge lids 40 that are additionally provided on end faces of the core member 10 on the insertion sides and tightly contact with an inner wall of the container main unit 3 at an outer peripheral face to perform such a function as positioning or fixing of the core member 10.

The container main unit 3 is formed from a resin material having a desired thickness and an accordion portion 3A obtained by connecting a plurality of annular stepped portions 3a continuously formed on an outer peripheral face of the container main unit 3 in a range of about half length thereof so as to extend in a longitudinal direction. An annular groove portion (a small diameter portion) 3b is formed in a boundary portion between adjacent annular stepped portions 3a. An inner wall of the container main unit 3 inside the accordion portion 3A is formed in a corrugated shape reflecting the shapes of the annular stepped portions 3a and the annular groove portions 3b.

Upper faces of the respective caps 5a and 5b made from a resin material are formed in flat faces suitable for stationary placement on a flat place. Accordingly, the container main unit 3 closed by the caps 5a and 5b can be placed upright on a flat place such that either of the caps 5a and 5b faces downwardly. Therefore, by placing the container main unit upright on a disk or the like such that the cap on the insertion recess side to be used in first faces downwardly, lubricating liquid charged in the respective insertion recesses 12a and 12b can lubricate a portion near the inlet of the insertion recess to be used at first. Thus, penis insertion can be made smoother. On the other hand, by temporarily closing the respective insertion ports 11a and 11b using lid plates 35 described later, leakage of lubricating liquid can be prevented.

A small hole for degassing is preliminarily formed at a proper portion on the upper face of each of the caps 5a and 5b as necessary and it is preliminarily sealed in the unused state by a seal (not shown). The seal is removed when it is used and a tight contact degree or a tight contact feeling between the inner wall of the core member 10 and a penis can be adjusted by opening and closing the small hole during use with a user's finger. That is, since the penis tightly contacts with the inner wall of the core member 10 in a closed state of the small hole, a tightening force becomes strong, while the tightening force becomes weak in an opened state of the small hole. It is made possible to fluctuate the tightening force to fluctuate stimulations according to a simple operation such as merely opening and closing the small hole. When a user feels pain in his penis, he can open the small hole.

The core member 10 is a bag-like member made from gel-like resin, gel-like rubber having viscosity, or the like, such as elastomer, it includes a core main unit 10A having two independent insertion rooms 12a and 12b that do not communicate with each other therein and large-diameter flanges 10B and 10B fixed to both end faces of the core member 10A in a longitudinal direction, and small-diameter insertion ports 11a and 11b are formed at central portions of the respective flanges 10B and 10B. Insertion rooms 12a and 12b having diameters larger than those of the respective insertion ports are formed to communicate with the insertion ports inside the respective insertion rooms 12a and 12b. A projecting portion (s), a fold(s), or the like is formed inside each of the insertion rooms 12a and 12b with arbitrary arrangement. A proper amount of lotion serving as lubricating liquid or the like is preliminarily charged in the insertion rooms 12a and 12b.

As shown in FIG. 20, a partition wall 10C for partitioning the respective insertion rooms 12a and 12 such that the rooms do not communicate with each other is disposed in the cylindrical core main unit 10A. The partition wall 10C defines the two insertion rooms 12a and 12b in the core main unit 10A by integrating both end portions of the partition wall 10C in the longitudinal direction to the inner walls of the respective flange portions 10B and 10B (so as not to close the respective insertion ports) and integrating the both end portions thereof in a widthwise direction to the inner wall of the core main unit 10A.

Respective outer walls of the respective insertion rooms 12a and 12b tightly contact with the sponge layer 20 so that their deformations (expansions in outer diametrical directions) are suppressed, while an inner side of each insertion room, namely, the partition wall 10C can be elastically deformed toward the other insertion room. Accordingly, a feeling obtained when a penis is rubbed on an outer wall of each insertion room is significantly different from a feeling obtained when the penis is rubbed on the partition wall 10C. Utilizing the special structure, a user can select either of the outer wall imparting hard (hardly deformed to the outside) feeling and the partition wall 10C imparting soft feeling as a portion on which a sensitive portion of his glans of penis rubs arbitrarily to create a use method satisfying his liking.

By making the inner diameters of the respective insertion rooms 12a and 12b different or changing shapes of projecting portions or folds projecting from the inner wall, the number thereof, or the like, different feelings can be obtained.

Since the stepped inner wall of the accordion portion 3A of the container main unit 3 presses an outer face of the core member 10 via the sponge layer 20 to pressure-hold an outer peripheral face of the core member 10, a corresponding portion of the core member 10 is always put in a pressed state by the accordion portion 3A, so that a shape-holding force of the core member 10 is increased and buckling of the core member 10 is prevented at a forcible penis insertion or during penis rubbing.

Plate-like ribs 14 extending in an axial direction are also integrally formed on an outer peripheral face of the core member 10. The ribs 14 can be ribs extending in a circumferential direction.

A short cut line 15 for degassing serving as a check valve is formed by cutting at a proper point on a distal end portion of each of the insertion recesses 12a and 12b of the core member 10 in advance. Since the cut line 15 is completely closed in a non-insertion state of a penis according to an elastic force of the core member itself, lubricating liquid inside the core member 10 is prevented from leaking and when an internal pressure is raised due to penis insertion, the air that tends to be accumulated between a penis distal end and an inner bottom face of each of the insertion rooms 12a and 12b can be degassed by opening the cut line 15. After the air is removed, even if an operation for rubbing of the penis is performed, the cut line 15 is kept to close so that lubricating liquid hardly flows to the outside. However, even if a small amount of lubrication liquid leaks from the cut line 15, there will not be such a state that lubricating liquid inside the core member 10 lacks to such an extent that the shortage disturbs use of this apparatus.

By arranging a lid plate 35 that tightly contacts with each end face of the core member 10 around a peripheral edge of each of the insertion ports 11a and 11b at each insertion port of the core member to openably/closably close the insertion port to close the insertion port, lubricating liquid charged in the insertion room 12 is prevented from leaking. Accordingly, even when the container 2 is placed such that either of the caps 5a and 5b sides faces downwardly, lubricating liquid does not leak, so that the insertion port side of each of the insertion rooms 12a and 12b can be maintained in sufficiently-lubricated state. Also, reduction of lubricating liquid inside the core member 10 due to drying is prevented owing to presence of the lid plate 35. Drying inside the core member 10 is further prevented by impregnation of lubricating liquid in the sponge lid 40.

An effect can be obtained that the lid plate 35 on the upper side serves to prevent drying inside the insertion room, while the lid plate 35 on the lower side serves to accumulate the lotion near the insertion portion. Even if a lid pair is provided on only the lower portion, lotion is distributed into the insertion recess on the upper side according to insertion from the lower portion so that a state where a penis can be easily inserted with excellent lubrication can be achieved.

Since the lid plate 35 is made from a gel-like resin equal to the material for the core member 10, it tightly contacts with each insertion side end face of the core member 10 to seal each of the insertion ports 11a and 11b. On the other hand, when a penis is inserted to the insertion port, the lid plate 35 is pushed into the insertion port by a penis distal end, and it does not disturb rubbing operations performed thereafter. On the contrary, since the lid plate 35 is interposed between his glans of penis and the inner wall of the insertion room, irregular stimulations can be imparted to the glans of penis so that a sperm collecting efficiency can be, improved.

A cut line 41 for penis insertion is formed in the sponge lid 40 additionally provided on a face of each of the flanges 10B and 10B of the core member 10 in advance, but when each of the insertion ports 11a and 11b is closed from the outside using the lid plate 35, a hole 42 fitted with the lid 35 can be formed at a central portion of the sponge lid 40 in advance. Thereby, an inside face of the sponge lid 40 can be caused to tightly contact with the face of each of the flanges 10B and 10B, so that a force for positioning and fixing the core member 10 increases owing to the sponge lid 40. The force for fixing the lid plate 35 also increases.

When the sponge lid 40 having the cut line 41 is interposed between the end face of the core member 10 at the insertion port side and the cap 5, as also shown in FIG. 18 and FIG. 20, a portion of the sponge lid 40 is protruded beyond the end edge of the opening portion of the container main unit 3 to the outside by a predetermined amount (for example, 3 mm to 5 mm). By adopting such a configuration, a drawback such that due to repetitive abutting of an opening portion peripheral edge of the container main unit on a proximal portion of user's penis or skin around his penis during use of the container main unit, a portion of the user on which the opening portion peripheral edge abuts is injured or the user feels discomfort about the use, can be eliminated.

Next, the sponge layer 20 is made of a foam resin sheet but is not a simple sheet, and is formed with a holding portion 21 holding a rib 14 formed on the outer periphery of the core member to prevent buckling of the core member. In this embodiment, an example that two plate-like ribs 14 extending in an axial direction are provided is shown, where in order to hold these ribs 14, the core member 10 and the sponge layer 20 are integrated by providing the holding portion 21 formed as a cut line extending in the axial direction in an intermediate portion of the sponge layer 20 in a circumferential direction to hold one rib 14 in the holding portion 21 and to hold the other rib 14 between both end faces of the sponge layer 20 in the circumferential direction. The integrated core member 10 and sponge member 20 are inserted into the container main unit 3 from the opening portion 4 side (FIG. 22).

When there are three or more ribs 14, the number of holding portions 21 is increased correspondingly. When a forming direction of the rib 14 is a circumferential direction or another direction, a forming direction of the holding portion is changed similarly.

Based on such a contraption as variation of the thickness of the sponge layer 20 along the longitudinal direction of the core member 10, variation thereof along the circumferential direction, arrangement of a projection(s) on an inner face of the sponge layer 20, and the like, pressure to the core member 10 from the peripheral face can be fluctuated so that stimulations to a penis are fluctuated and increased.

In use of the sperm collecting apparatus, while a user inserts his penis into the insertion room from one opening portion to use the apparatus, the other opening portion is closed by the cap and the sponge lid 40. Therefore, since the elastically compressible sponge lid that is backed up by the cap is always present on the distal end side of one insertion room during use of the one insertion room, a difference in penis size can be accommodated. That is, when a penis length is shorter than a standard size, the sponge lid positioned at the distal end side of the insertion room in use receives the distal end of the core member 10 to prevent collapse and deformation of a distal end shape of the core member 10 and maintains a rubbing force to a penis distal end, while when the penis length is longer than the standard length, the sponge lid positioned at the distal end side of the core member 10 is compressed and deformed by the penis distal end to be capable of maintaining the rubbing force between the distal end of the core member 10 and the penis distal end sufficiently.

After ejaculation utilizing one insertion room has been finished, the opening portion corresponding to the insertion room is closed by the sponge lid and the cap, so that leakage of liquid inside the insertion room is prevented. Since the insertion room on an unused side is utilized in the next use, the sponge-lid on the used side serves as a cushion so that the difference in penis size can be accommodated.

In the above embodiment, the example where diameters of both end portions of the container 2 in the longitudinal direction are almost the same has been described. However, the entire or a portion of the container main unit 3 can be formed in an oval shape, an elongated oval shape or the like, or a flat shape.

In this invention, since common specification can be respectively applied to the lid plates 35 and the sponge lids 40, cost reduction can be achieved.

Figure 23:
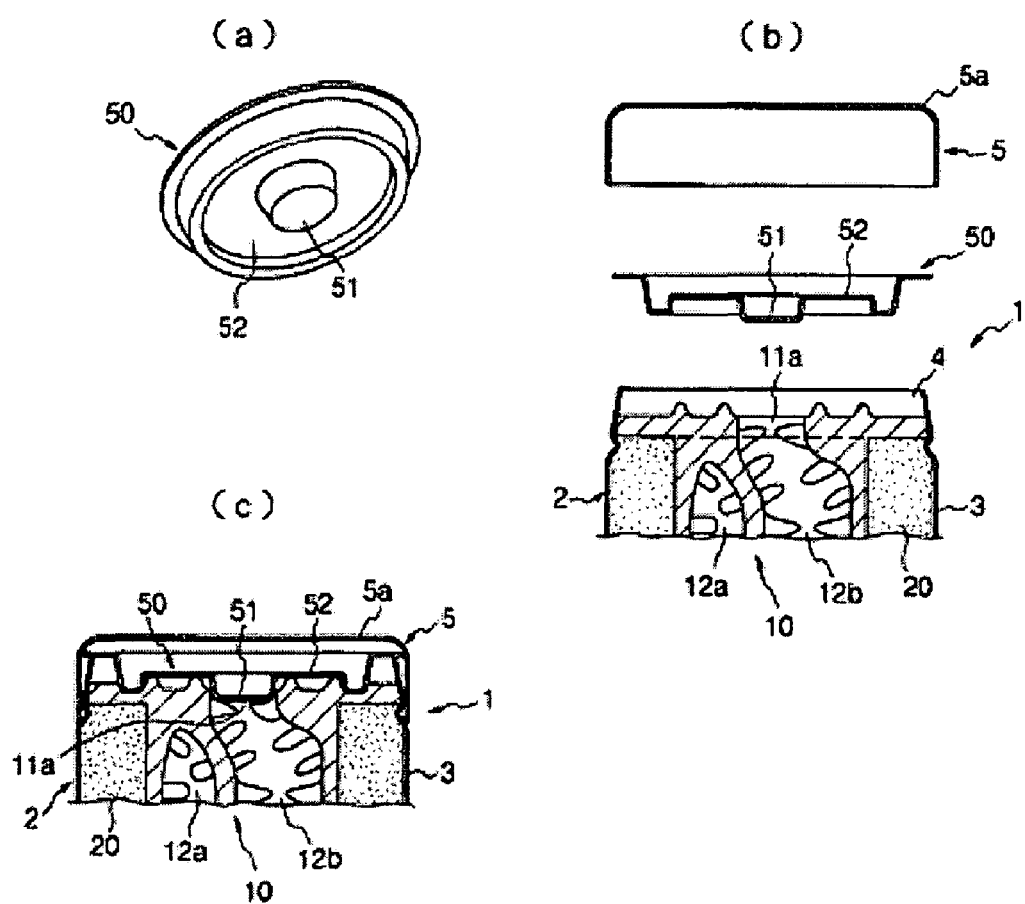
FIGS. 23(a), 23(b) and 23(c) are a configuration diagram of an inner cap used in a sperm collecting apparatus according to another embodiment of the present invention, a vertical sectional view of main parts before the inner cap is attached thereto, and a vertical sectional view after the inner cap has been attached thereto.

Next, FIGS. 23(*a*), 23(*b*) and 23(*c*) are a configuration diagram of an inner cap used in a sperm collecting apparatus according to another embodiment of the third invention, a vertical sectional view of main parts of the sperm collecting apparatus before the inner cap is attached, and a vertical sectional view of the sperm collecting apparatus after the inner cap has been attached. Like portions as those in the sperm collecting apparatus according to the respective embodiments described above are attached with like reference numerals in the following explanation.

The sperm collecting apparatus according to this embodiment includes an inner cap 50 having a projecting portion 51 that is fitted to either one of insertion ports 11*a* and 11*b* provided in both end faces of the core member 10 in an axial direction from the outside to close the either one of the insertion ports 11*a* and 11*b* and a supporting face (a supporting plate) 52 that supports the projecting portion 51 and contacts with at least one end face of the core member 10 in a longitudinal direction thereof. The inner cap 50 is formed of, for example, a resin plate (a material harder than a constituent material for the core member or the sponge) thinner than the container main unit 3, and the projecting portion 51 is pressure-fitted into the either one of the insertion ports 11*a* and 11*b*, so that the projecting portion 51 is caused to tightly contact with an inner peripheral face of the insertion port to prevent leakage of lotion inside the core member. Since the projecting portion 51 is harder than a constituent material for the core member 10, it tightly contacts with and fitted into each insertion port to be capable of preventing leakage of lotion and attaching and detaching operations to/from the insertion port can be performed smoothly. The supporting face 52 expanding from an outer peripheral edge of the projecting portion 51 in an outer diametrical direction tightly contacts with at least one portion of the front end face of the core member 10 to serve to prevent spread or outflow of lotion in the outer diametrical direction even if the lotion leaks. Further, since an outer peripheral edge of the supporting face 52 tightly contacts with (or is preliminarily integrated with) an inner peripheral face of the cap 5, the whole inner cap 50 is pressure-contacted with the front end face of the core member 10, when the cap 5 is closed, so that positional deviation is prevented and lotion leakage is not occurred.

In this embodiment, it is preferable that a space for accumulating lotion for insertion as shown in FIG. 9 is provided.

Figure 24:
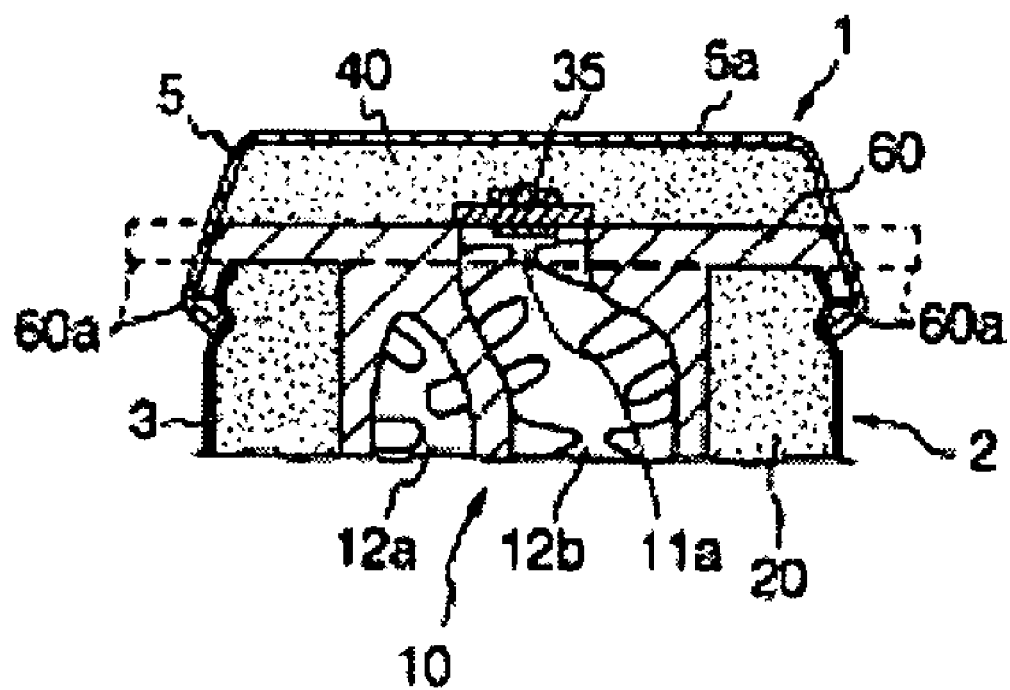
FIG. 24 is a sectional view showing a configuration of a sperm collecting apparatus according to another embodiment of the present invention.

Next, FIG. 24 is a sectional view showing a configuration of a sperm collecting apparatus according to another embodiment of the third invention. In the sperm collecting apparatus according to this embodiment, a disk-like flange portion 60 is formed on at least one end face of the core member 10 in a longitudinal direction (an axial direction), an outer peripheral edge 60*a* of the flange portion 60 made from a soft material is formed in a large diameter so as to bulge beyond the opening portion 4 of the container main unit 3 in an outer diametrical direction, and an end edge 4*a* of the opening portion 4 of the container main unit is covered with the outer peripheral edge 60*a* of the flange portion 60 made from a soft material so that the outer peripheral edge 60*a* of the flange portion 60 is held in a state that it has been folded outside the opening portion 4 such that a portion of a human body does not directly contact with the end edge 4*a*. The outer peripheral edge 60*a* of the flange portion 60 is preferably bonded to an outer face of the opening portion 4 in a state that the outer peripheral edge 60*a* has been pushed back to the outside of the opening portion 4.

With this configuration, when a user detaches the cap 5 to expose the front end face of the core member 10 and inserts his penis into the insertion port 11 to conduct a rubbing operation, he is prevented from feeling pain due to contact of the end edge 4*a* of the opening portion with his lower abdomen. The outer peripheral edge 60*a* is prevented from being peeled off during use by bonding the outer peripheral edge 60*a* of the folded flange portion 60 to the outer face of the opening portion in advance.

Also in this embodiment, the outer peripheral edge 60*a* of the flange portion 60 can be pressed by an annular pressing member such as shown in FIG. 10.

The inner cap according to the embodiment shown in FIG. 23 can be applied to the embodiment shown in FIG. 24.

What is claimed is:

1. A sperm collecting apparatus comprising:
a container having a non-cylindrical container main unit comprising an end face and a cap that is attachable to an opening portion of the container main unit;
a core member made from a gel-like material, that is located in said container main unit and has an insertion room extending to an inner portion of the core member from an insertion port located at the end face;
a sponge layer which is interposed between said core member and an inner wall of said container main unit; and
a flange portion formed at one end face of said core member, an outer peripheral edge of the flange portion bulging beyond the opening portion of said container main unit in an outer diametrical direction,
where said container main unit is a non-cylindrical member with an intermediate portion in a longitudinal direction thereof having an outer diameter smaller than those in both end portions thereof in the longitudinal direction, an upper face of said cap is a substantially flat face, and an end portion of said container main unit opposed to said opening portion is formed in a substantially arc face.

2. The sperm collecting apparatus according to claim 1, where an inner diameter of the insertion room of said core member corresponding to said small diameter portion provided on the intermediate portion of said container main unit is smaller than an inner diameter of another portion of the insertion room.

3. The sperm collecting apparatus according to claim 1, where an outer diameter of an end portion of said non-cylindrical container main unit at a depth side is smaller than that of an end portion thereof at said opening portion side.

4. The sperm collecting apparatus according to claim 1, where said core member includes a projecting rib projecting on an outer peripheral face thereof; and
said sponge layer includes a holding portion which contacts said rib.

5. The sperm collecting apparatus according to claim 1, further comprising a sponge lid having a cut is interposed between an end face of said core member at the insertion port side and said cap, with a portion of the sponge lid protruding beyond an end edge of the opening portion of said container main unit.

6. The sperm collecting apparatus according to claim 1, further comprising a cut line is formed in a distal end portion of said core member.

7. The sperm collecting apparatus according to claim 1, further comprising a bottom portion sponge layer is interposed between an inner bottom face of said container main unit and a distal end face of said core member.

8. The sperm collecting apparatus according to claim 1, further comprising an inner cap having a projecting portion which is fittable in the insertion port of said core member.

9. The sperm collecting apparatus according to claim 8, further comprising a room for accumulating lotion is formed between the supporting face of said inner cap and one end face of said core member.

10. The sperm collecting apparatus according to claim 1, wherein the outer peripheral edge of said flange portion is kept in an outwardly-folded state such that the outer peripheral edge of the flange portion covers an end edge of the opening portion of said container main unit.

11. A sperm collecting apparatus comprising:
a container having a non-cylindrical container main unit comprising an end face and a cap that is attachable to an opening portion of the container main unit;
a core member made from a gel-like material, that is located in said container main unit and has an insertion room extending to an inner portion of the core member from an insertion port at the end face;
a sponge layer which is interposed between said core member and an inner wall of said container main unit; and
a flange portion formed at one end face of said core member, an outer peripheral edge of the flange portion bulging beyond the opening portion of said container main unit in an outer diametrical direction,
where an outer shape of said non-cylindrical container is formed such that the end face of said non-cylindrical container at the opening portion side is a substantially circular flat face, a side face width is gradually decreased toward an intermediate portion in a longitudinal direction thereof, and a side face width of the depth end portion is minimized.

12. A sperm collecting apparatus comprising:
a container comprising a cylindrical container main unit having an end in a longitudinal direction that is substantially open and a cap that is attachable to an opening portion of the container main unit;
a core member made from a gel-like material, which is located in said container main unit and has an insertion room extending to an inner portion of the core member from an insertion port at an end face in a longitudinal direction in the core member;
a sponge layer which is interposed between said core member and an inner wall of said container main unit; and
a flange portion formed at one end face of said core member, an outer peripheral edge of the flange portion bulging beyond the opening portion of said container main unit in an outer diametrical direction,
where the container main unit includes a deformable portion more deformable than another portion at a proper portion in an intermediate portion in the longitudinal direction.

13. The sperm collecting apparatus according to claim 12, where the core member includes a projecting rib projecting on an outer peripheral face thereof; and said sponge layer includes a holding portion which contacts said rib.

14. A sperm collecting apparatus comprising:
a container comprising a non-cylindrical container main unit whose both end faces in a longitudinal direction are substantially open and two caps that are attachable to respective opening portions of the container main unit;
a core member made from a gel-like material, which is located in said container main unit and has at least two insertion rooms extending to an inner portion of the core member from insertion ports provided in both end faces of the core member in a longitudinal direction in the core member;
a sponge layer which is interposed between said core member and an inner wall of said container main unit; and
a flange portion formed at one end face of said core member, an outer peripheral edge of the flange portion bulging beyond the opening portion of said container main unit in an outer diametrical direction.

15. The sperm collecting apparatus according to claim 14, where said non-cylindrical container main unit has a small-diameter portion on a proper outer face of at least one portion.

16. The sperm collecting apparatus according to claim 14, where an inner diameter of each of the two insertion rooms of said core member are different from each other.

17. The sperm collecting apparatus according to claim 14, where at least two sponge lids having a cut are located between both end faces of said core member and inner faces of said respective caps.

18. The sperm collecting apparatus according to claim 17, where a portion of said sponge lid is protruded beyond an end edge of the opening portion of said container main unit.

19. The sperm collecting apparatus according to claim 14, where said core member includes a projecting rib projecting on an outer peripheral face thereof; and
said sponge layer includes a holding portion which contacts said rib.

20. The sperm collecting apparatus according to claim 14, further comprising a cut line formed on a proper portion at a distal end portion of said core member.

21. The sperm collecting apparatus according to claim 14 further comprising an inner cap having a projecting portion which is fitted in at least one insertion port of said core member from the outside to close the one insertion port and a supporting face which supports said projecting portion and contacts with one end face of said core member in the longitudinal direction.

22. The sperm collecting apparatus according to claim 21, further comprising a space for accumulating lotion for is formed between the supporting face of said inner cap and one end face of said core member.

23. The sperm collecting apparatus according to claim 14, wherein the outer peripheral edge of the flange portion is kept in an outwardly-folded state such that the outer peripheral edge of the flange portion covers an end edge of the opening portion of said container main unit.

* * * * *